(12) United States Patent
Lee

(10) Patent No.: US 9,593,318 B2
(45) Date of Patent: Mar. 14, 2017

(54) LINKER-BRIDGED GENE OR DOMAIN FUSION REVERSE TRANSCRIPTASE ENZYME

(71) Applicant: Jun Euihum Lee, San Diego, CA (US)

(72) Inventor: Jun Euihum Lee, San Diego, CA (US)

( * ) Notice: Subject to any disclaimer, the term of this patent is extended or adjusted under 35 U.S.C. 154(b) by 47 days.

(21) Appl. No.: 13/870,842

(22) Filed: Apr. 25, 2013

(65) Prior Publication Data

US 2014/0322789 A1    Oct. 30, 2014

(51) Int. Cl.
*C12N 9/12* (2006.01)
*C12N 9/22* (2006.01)

(52) U.S. Cl.
CPC .............. *C12N 9/22* (2013.01); *C12N 9/1241* (2013.01); *C12Y 207/07049* (2013.01); *C07K 2319/00* (2013.01)

(58) Field of Classification Search
None
See application file for complete search history.

(56) References Cited

U.S. PATENT DOCUMENTS 6,271,004 B1 *   8/2001   Warthoe .................... 435/91.51

OTHER PUBLICATIONS

Tanese and Goff Proccedings of the National Academy, vol. 85, pp. 1777-1781, 1988.*
Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard Hutson
(74) *Attorney, Agent, or Firm* — East West Law Group; Heedong Chae

(57) ABSTRACT

The present invention relates to combinations of a linker bridged gene or domain fusion reverse transcriptase enzyme, and more particularly, combinations of a linker bridged gene or domain fusion reverse transcriptase enzyme and their fusion construction utilizing for more efficient and quality DNA synthesis in reverse transcription. The composition of the invention includes a polymerase domain; a linker, consisting of 3-40 amino acids; and an RNase H domain, wherein the RNase H domain is either unmodified or modified with point mutations. The composition may further include another mutated RNase H, a mutated RNase A, and an additional linker which consists of 3-40 amino acids.

1 Claim, 12 Drawing Sheets

LINKER-BRIDGED GENE OR DOMAIN FUSION REVERSE TRANSCRIPTASE ENZYME

CROSS REFERENCE TO RELATED APPLICATIONS

This application claims priority to Provisional Application Ser. No. 61/638,463, filed Apr. 25, 2012, the contents of which are incorporated herein by reference in their entirety.

FIELD

The present invention relates to combinations of a linker bridged gene or domain fusion reverse transcriptase enzyme, and more particularly, combinations of a linker bridged gene or domain fusion reverse transcriptase enzyme and their fusion construction utilizing for more efficient and quality DNA synthesis in reverse transcription.

BACKGROUND

Reverse transcription is a critical step in the life cycle of all RNA tumor viruses, also known as retroviruses because the retroviruses integrate their DNA into the host cell DNA by a reverse transcriptase (RT), also known as an RNA-dependent DNA polymerase, wherein the RT directs the synthesis of a complementary DNA (cDNA) from an RNA template.

An RT is a DNA polymerase enzyme that is encoded by retroviruses, which use the enzyme during the process of replication. Reverse-transcribing RNA viruses, such as retroviruses, use the enzyme to reverse-transcribe their RNA genomes into DNA, which is then integrated into the host genome and replicated along with it. The virus thereafter replicates as part of the host cell's DNA. Without reverse transcriptase, the viral genome would not be able to incorporate into the host cell, resulting in the failure of the ability to replicate.

Both viral and cloned RTs contain two enzymatic activities: DNA polymerase activity and ribonuclease H (RNase H) activity. In the retrovirus life cycle, DNA polymerase activity is responsible for transcribing viral RNA into double-stranded DNA. RNase H activity, on the other hand, degrades RNA from RNA-DNA hybrids, such as are formed during reverse transcription of an RNA template.

Retroviral RNase H, a part of the viral reverse transcriptase enzyme, is an important pharmaceutical target, as it is absolutely necessary for the proliferation of retroviruses, such as HIV and murine leukemia virus (M-MLV). Mizuno, M., Yasukawa K, Inouye K. Insight into the Mechanism of the Stabilization of Moloney Murine Leukemia Virus Reverse Transcriptase by Eliminating RNase H activity. Biosci. Biotechnol. Biochem. 74 (2):440-2 (2010); Coté M L, Roth M J. Murine leukemia virus reverse transcriptase: structural comparison with HIV-1 reverse transcriptase. Virus Res. 134 (1-2): 186-202 (2008).

As a result, RT is used extensively in recombinant DNA technology to synthesize cDNA from mRNA. One major problem with cDNA synthesis is that the RNase H activity of RT degrades the mRNA template during first-strand synthesis. The mRNA poly(A)-oligo(dT) hybrid used as a primer for first-strand cDNA synthesis is degraded by RT RNase H. Thus, at the outset of cDNA synthesis, a competition is established between RNase H-mediated deadenylation of mRNA and initiation of DNA synthesis, which reduces the yield of cDNA product, Berger, S. L., et al., Biochem. 22:2365-73 (1983), and often causes premature termination of DNA chain growth.

Accordingly, a need for developing conditions, which are more efficient for supporting cDNA synthesis, sequencing, and amplification in reverse transcription, has been present for a long time. This invention is directed to solve these problems and satisfy a long-felt need.

SUMMARY OF THE INVENTION

The present invention contrives to solve the disadvantages of the prior art. The present invention provides a composition of a gene or domain RT, having a linker or linkers consisting of 3-40 amino acids. In one embodiment of the present invention, RNase H domain of the gene or domain RT may be either unmodified or modified with point mutations.

The object of the invention is to provide a composition of a gene or domain RT, comprising a polymerase domain, a first RNase H domain, a second RNase H which is mutated, and a linker, wherein the first RNase H domain is either unmodified or modified with point mutations.

Still another object of the invention is to provide a composition of a gene or domain RT with RNase H domain deletion, comprising a mutated RNase H, and a linker.

Still another object of the invention is to provide a composition of a gene or domain RT, comprising a polymerase domain, an RNase H domain, a mutated RNase A, and a linker, wherein the RNase H domain is either unmodified or modified with point mutations.

Still another object of the invention is to provide a composition of a gene or domain RT, comprising a polymerase domain, a first RNase H domain, a second RNase H which is mutated, a mutated RNase A, and two linkers, wherein the first RNase H domain is either unmodified or modified with point mutations.

Still another object of the invention is to provide a composition of a gene or domain RT with RNase H domain deletion, comprising a mutated RNase H, a mutated RNase A, and two linkers.

The advantages of the present invention include that (1) the present invention provides novel compositions of a gene or domain fusion reverse transcriptase (RT) which is more efficient for DNA synthesis in reverse transcription; (2) the present invention provides a gene or domain fusion RT which exhibits slow dissociation from RNA-primers and/or RNA-DNA hybrids due to its higher affinity to the RNA-primers and the RNA-DNA hybrids; (3) the present invention provides a gene or domain fusion RT which exhibits higher processivity, higher DNA yield, higher DNA quality, longer DNA chain extension and higher DNA replication fidelity in reverse transcription; (4) the present invention provides a gene or domain fusion RT which exhibits higher temperature performance which in turn contributes to high yields of quality full length cDNA with full gene representation; (5) the present invention further provides a method of producing cDNA from mRNA using the a linker bridged gene or domain fusion enzyme of the present invention; and (6) the present invention also provides a kit for the preparation of cDNA from mRNA comprising the linker bridged gene or domain fusion enzyme of the present invention.

Although the present invention is briefly summarized, the fuller understanding of the invention can be obtained by the following drawings, detailed description and appended claims. It should be understood, however, that the detailed description and the specific examples, while indicating preferred embodiments of the invention, are given by way of

BRIEF DESCRIPTION OF THE DRAWINGS

FIG. 3-1 shows cDNA synthesis activity of fusion RT of the present invention;

FIG. 3-2 shows purified fusion RT of the present invention;

FIG. 3-3 shows cDNA synthesis activity of fusion RT of the present invention;

FIG. 3-4 shows processivity of fusion RT of the present invention;

DETAILED DESCRIPTION OF THE INVENTION

Figure 1A:
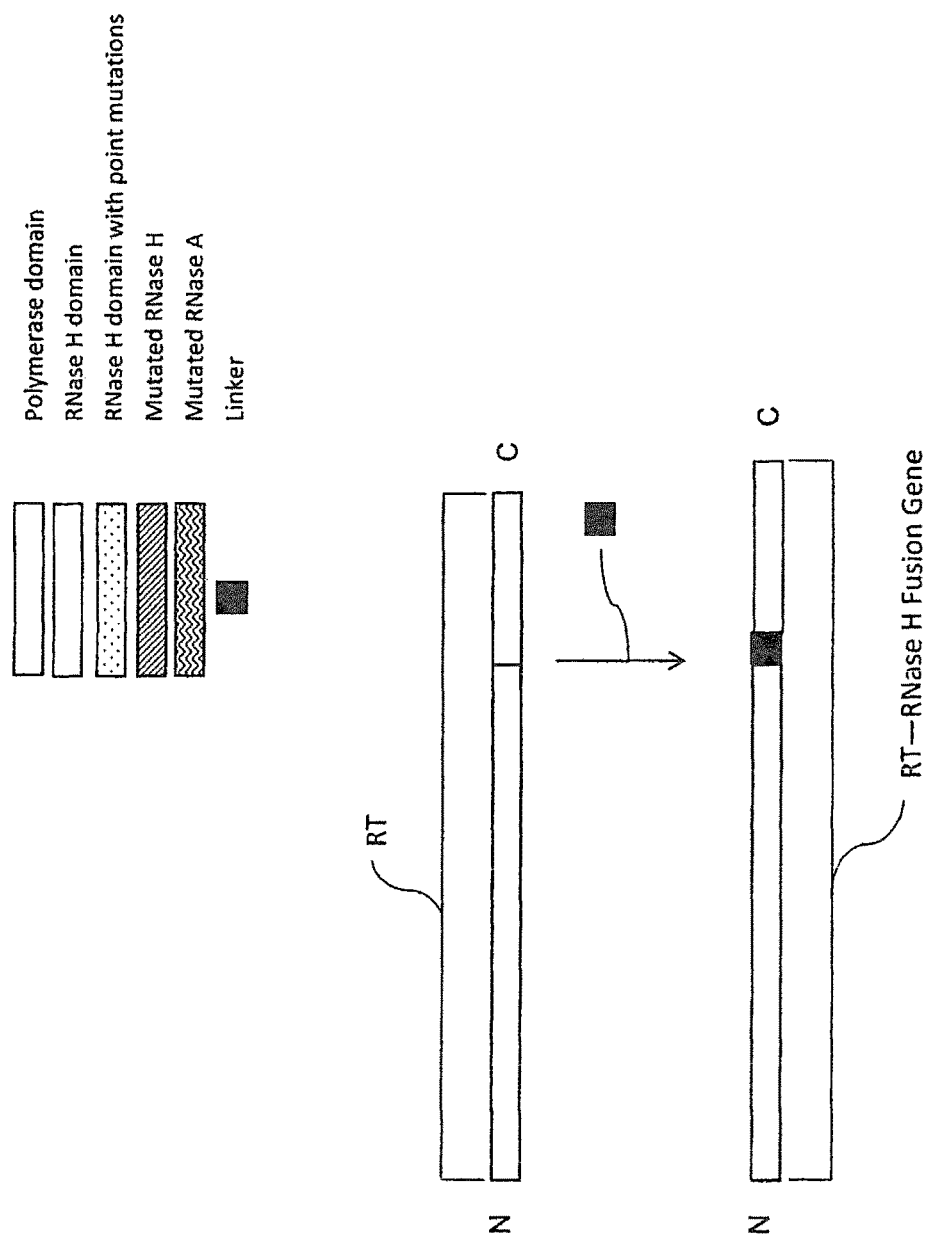
FIG. 1A illustrates a transition from an unmodified RT to a linker-bridged gene fusion RT according to the present invention, wherein in frame N-terminal polymerase domain and in frame C-terminal RNase H domain are fused by a linker.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

An "RT with point mutations" as defined herein, is a genetically engineered reverse transcriptase enzyme which exhibits reduced RNase H activity by the introduction of point mutations.

An "RT with RNase H deletion" as defined herein, is a genetically engineered reverse transcriptase enzyme comprising only polymerase domain after RNase H domain being removed by a C-terminal deletion.

A "mutated RNase H" as defined herein, is a genetically engineered RNase H which exhibits reduced or no RNase H activity that degrades RNA from RNA-DNA hybrids by point mutations.

A "mutated RNase A" as defined herein, is a genetically engineered RNase A which exhibits reduced or no RNase A activity that cleaves single-stranded RNA by point mutations.

"Point mutation" as defined herein, refers to a base-pair mismatch, i.e., any base-pairing other than any of the normal A:T(U) and C:G pairs. Non-limiting examples of base-pair mismatch include A:A, A:C, A:G, C:C, C:T, G:G, G:T, T:T, C:U, G:U, T:U, U:U, 5-formyluracil (fU):G, 7,8-dihydro-8-oxo-guanine (8-oxoG):C, 8-oxoG:A.

Reverse Transcriptase

The reverse transcriptase (RT) gene (or the genetic information contained therein) can be obtained from a number of different sources. For instance, the gene may be obtained from eukaryotic cells which are infected with retrovirus, or from a number of plasmids which contain either a portion of or the entire retrovirus genome. In addition, messenger RNA-like RNA which contains the RT gene can be obtained from retroviruses. Examples of sources for RT include, but are not limited to, Moloney murine leukemia virus (M-MLV); human T-cell leukemia virus type 1 (HTLV-1); bovine leukemia virus (BLV); Rous Sarcoma Virus (RSV); human immunodeficiency virus (HIV); yeast, including *Saccharomyces, Neurospora, Drosophila*; primates; and rodents. See, for example, Weiss, et al., U.S. Pat. No. 4,663,290 (1987); Gerard, G. R., DNA:271-79 (1986); Kotewicz, M. L., et al., Gene 35:249-58 (1985); Tanese, N., et al., Proc. Natl. Acad. Sci. (USA):4944-48 (1985); Roth, M. J., at al., J. Biol. Chem. 260:9326-35 (1985); Michel, F., et al., Nature 316:641-43 (1985); Akins, R. A., et al., Cell 47:505-16 (1986), EMBO J. 4:1267-75 (1985); and Fawcett, D. F., Cell 47:1007-15 (1986).

Mutated Ribonuclease H

Computer analysis of the amino acid sequences from the putative gene products of retroviral pol genes has revealed a 150-residue segment at the carboxyl terminus that is homologous with the ribonuclease H of *E. coli* and a section close to the amino terminus which can be aligned with nonretroviral polymerases. Johnson, M. S., et al., Proc. Natl. Acad. Sci. (USA) 83:7648-52 (1986). Based on these related amino acid sequences, Johnson, at al. suggest that RNase H activity should be situated at the carboxyl terminus, and the DNA polymerase activity at the amino terminus.

In another example, the Moloney murine leukemia virus (M-MLV) enzyme, the DNA polymerase and RNase H activities reside in physically separable domains of a single monomeric protein. Tanese, N., et al., Proc. Natl. Acad. Sci. USA 85:1777-81 (1988).

It has been reported that elimination or profound reduction of RNase H activity in the murine system may occur in a series of mutants of M-MLV with linker-insertion mutations in the RT region of the pol gene. Tanese, N., et. al., J. Virol. 65:4387-97 (1991). It has been reported that reverse transcriptase gene having DNA polymerase activity and substantially no RNase H activity that could yield more full length cDNA without significant degradation of the mRNA template during first strand synthesis. (U.S. Pat. Nos. 5,244, 797 and 5,405,776).

It still remained unclear how RT's polymerase and RNase H activities can function coordinately. Some researchers have suggested that DNA synthesis and template degradation may occur contemporaneously and be performed by a single RT molecule during retroviral DNA synthesis. Schatz, O., et al., EMBO J., 9, 1171-1176 (1990); Peliska, J. A., et al., Science, 258, 1112-18 (1992). However, in reactions in vitro, RT's two activities can function separately (Champoux, 1993); that is, RNase H cleavages can occur in the absence of DNA polymerase activity and DNA polymerization can take place independently of RNase H degradation. Kinetic measurements of the relative rates of RT's DNA polymerase and RNase H activities in vitro suggest that DNA synthesis can proceed largely independently of RNase H action, suggesting that the two activities might function sequentially and involve separate RT molecules. Champoux, J. J. In Skalka, A. M. and Goff, S. P. (eds), Cold Spring Harbor, N.Y., pp. 103-17 (1993), Kati, W. M., et al., J. Biol. Chem., 267, 25988-97 (1992).

Therefore, the efforts to enhance DNA yield and DNA quality in reverse transcription by compensating the competition between RNase H-mediated deadnylation of mRNA and initiation of DNA synthesis have been focused on eliminating or reducing RNase H activity in RT.

In one example, RT genes having DNA polymerase activity and substantially no RNase H activity may be obtained by deletion of deoxyribonucleotides at the 3' end of the gene which encode the portion of the polypeptide having RNase H activity. Deletions of the RT gene may be accomplished by cutting the plasmid at selected restriction sites within the RT gene and discarding the excised fragment. Further deletion of consecutive deoxyribonucleotides may be accomplished by treating the fragment with an exonuclease. The DNA ends may then be joined in such a way that the translation reading frame of the gene is maintained. The plasmid thus obtained may then be used to transform hosts which may then be screened for altered RT activity. RT RNase H activity may be assayed according to Gerard, et al., J. Virol. 15:785-97 (1975). DNA polymerase activity may be assayed according to Gerard, et al., Biochem. 13:1632-41 (1974). Clones having DNA polymerase activity and substantially no RNase H activity may be used to prepare RT with altered activity. According to these methods, the portion of the RT gene derived from M-MLV which encodes DNA polymerase was localized to about 1495 base pairs (about 1018 to about 2512). The protein expressed by this gene has about 503 amino acids. This protein has DNA polymerase activity and substantially no RNase H activity.

The reverse transcriptase having DNA polymerase activity and substantially no RNase activity may be isolated according to conventional methods known to those skilled in the art. For example, the cells may be collected by centrifugation, washed with suitable buffers, lysed, and the reverse transcriptase isolated by column chromatography, for example, on DEAE-cellulose, phosphocellulose (see Kotewicz, et al., Gene 35:249-58 (1985)) or other standard isolation and identification techniques using, for example, polyribocytidylic acid-agarose, or hydroxylapatite or by electrophoresis or immunoprecipitation.

Another approach to enhance DNA yield and DNA quality in reverse transcription is to increase processivity of RT. Generally, RT exhibits low levels of processivity replicative DNA polymerase (Huber, et al., 1989; Katz and Salka, 1994). In typical in vitro assays with templates of random base composition retroviral RTs can extend a cDNA strand for only a few hundred nucleotides before dissociating. For example, M-MLV RT and avian myeloblastosis virus (AMV) RT can extend a cDNA strand for only 20-30 nucleotide and only few hundred nucleotides respectively before dissociating. Huber, H. E., McCoy, J. M., Seehra, J. S., and Richardson, C. C. J. Biol. Chem. 264, pp. 4669-78 (1989), Katz, R. A., and Skalka, A. M. Annu. Rev. Biochem. 63, pp. 133-173 (1994). Despite this low processivity has been suggested to be of advantage to the virus in-vivo because it promotes recombination between RNA templates, thus allowing faster rates of evolution for avoidance of the vertebrate host's immune system (Katz, R. A., and Skalka, 1990), such low processivity of RT has some limitation in cDNA synthesis application in vitro since it requires continuous reassociation of the RT with the RNA template before complete of full length cDNA.

For example, both M-MLV RT and AMV RT can extend a cDNA strand for only 20-30 nucleotide and only few hundred nucleotides respectively before dissociating. Huber, H. E., McCoy, J. M., Seehra, J. S., and Richardson, C. C. J. Biol. Chem. 264. pp. 4669-78 (1989), Katz, R. A., and Skalka, A. M. Annu. Rev. Biochem. 63, pp. 133-73 (1994). Yet, AMV RT exhibits higher processivity compared with M-MLV RT and that is a result of the slower rate of dissociation of the enzyme from RNA templates. AMV RT is also able to synthesize longer cDNA than M-MLV RT due to the higher processivity. The elongation rates of the two enzymes are similar. Bibillo A. and Eickbush, T. A, J. Biol. Chem., 277, pp. 34836-45 (2002).

Accordingly, slower dissociation and high affinity for RT can result in higher DNA yield, higher DNA quality, longer DNA chain extension and higher DNA replication fidelity in reverse transcription by increasing its processivity.

Mutated Ribonuclease A

On the other hand, Ribonuclease A (RNase A) is the most studied enzyme of the 20th century and is the best characterized ribonuclease. The "A" in its name refers not to its substrate specificity, but to the predominant form of the enzyme produced by the bovine pancreas. RNase A is unmodified, whereas RNase B, RNase C, and RNase D are mixtures of glycoforms. Because of its availability in large quantity and high purity, RNase A has been the object of landmark work in protein chemistry and enzymology. Cuchillo C M, Vilanova M, Nogués M V, Pancreatic ribonucleases, D'Alessio G, Riordan J F (eds) Ribonucleases: structures and functions, pp. 271-304, Academic Press, New York (1997). Bovine pancreatic ribonuclease A is a pyrimidine-specific ribonuclease, member of a large superfamily of homologous RNases. Beinterna J J, et al., Prog Biophys Mol. Biol. 51, pp. 165-92 (1988). The catalytic mechanism of RNase A has been studied in detail. Blackburn P, Moore S. Pancreatic ribonuclease, pp. 317-433. The enzymes, New York: Academic Press (1982).

RT synthesizes cDNA from primed-RNA template and result in RNA-DNA hybrid strand behind of RT enzyme and RNA strand is aligned in front of RT enzyme. Native RNase A is an RNA binding protein and degrades RNA.

RNase A catalyzes the cleavage of RNA in two subsequent reactions. The first reaction is a transesterification, which results in the cleavage of the P-05' bond at the 3' end of a pyrimidine, and the formation of a 2', 3' cyclic nucleotide. This cyclic nucleotide can be hydrolyzed in a second reaction. Chemical modification studies and analysis of the pH dependence of the enzymatic activity have shown that 2 histidines and 1 lysine are essential for enzymatic activity. Crestfield A M, et al., J. Biol. Chem., 238, pp. 2413-42 (1963). Findlay D., et al., Biochem J. 85, pp. 152-53 (1962).

RNase A (124 amino acids) can be truncated substantially without losing the ability to function as a specific enzyme. Synthesis of a 70-residue and three 63-residue analogs has revealed that several regions of the RNase polypeptide chain distant from the active site are not needed for the folding of the remainder of the molecule as shown by the agreement of the substrate specificities of natural enzyme and the synthetic analogs. Gutte, B. J., Biol. Chem. 250, pp. 889-904 (1975); Gutte, B. J., Biol. Chem. 252, pp. 663-70 (1977). Moreover, the 63-residue analogs had all three RNase A activities (transphosphorylating, synthetic, and hydrolytic), and they were bound by an affinity column specific for the active site fold of RNasc A. The 63-residue analogs could thus be considered RNase A models. Gutte, B. J., Biol. Chem. 252, pp. 663-670 (1977).

In one example, three amino acid residues located at the active site of RNase A (His12, Hisl119, and Lys41) are known to be involved in catalysis. Mutation of Hisl119 to asparagines was generated to study the role of His119 in RNase A catalysis. The mutation significantly decreases the rate of the transesterification reaction and has no effect on substrate affinity of the enzyme. Panov, Konstantin, FEBS Letters, vol. 398, pp. 57-60 (1996).

Linker

Accordingly, a mutated RNase H gene or domain fusion provides the high affinity to RNA-DNA hybrid strand which is behind of the RT enzyme and a mutated RNase A gene or domain fusion provides the high affinity to RNA strand which is in front of the RT enzyme by when the gene or domain fusion is using a linker or linkers. Such high affinity for RT can result in higher DNA yield, higher DNA quality, longer DNA chain extension and higher DNA replication fidelity in reverse transcription.

Certain embodiments provide compositions of a linker, wherein the linker consists of 3-40 amino acids. The optimum number of a linker for amino acids varies depending on target gene. The key is to provide enough flexibility for RT enzyme function but not too loosely.

For example, in one embodiment, a linker consists of 6 amino acids of SEQ ID NO. 7 or 8 (Ser-Ala-Ala-Gly-Val-Gly or Ala-Ala-Ala-Ala-Ala-Ala) and, in another embodiment, a linker consists of 18 amino acids of SEQ ID NO. 9 (Ser-Ala-Ala-Gly-Val-Gly-Ala-Ala-Gly-Gly-Ala-Ala-Ser-Ala-Ala-Gly-Val-Gly).

These examples are illustrative but not limiting of the methods and compositions of the present invention. Any suitable modifications, adaptations and improvements which are obvious to those skilled in the art are within the spirit and scope of the present invention.

Compositions and Examples

The following examples are illustrative but not limiting of the methods and compositions of the present invention. Any suitable modifications and adaptations which are obvious to one of ordinary skill in the art are within the spirit and scope of the present invention.

Figure 1B:
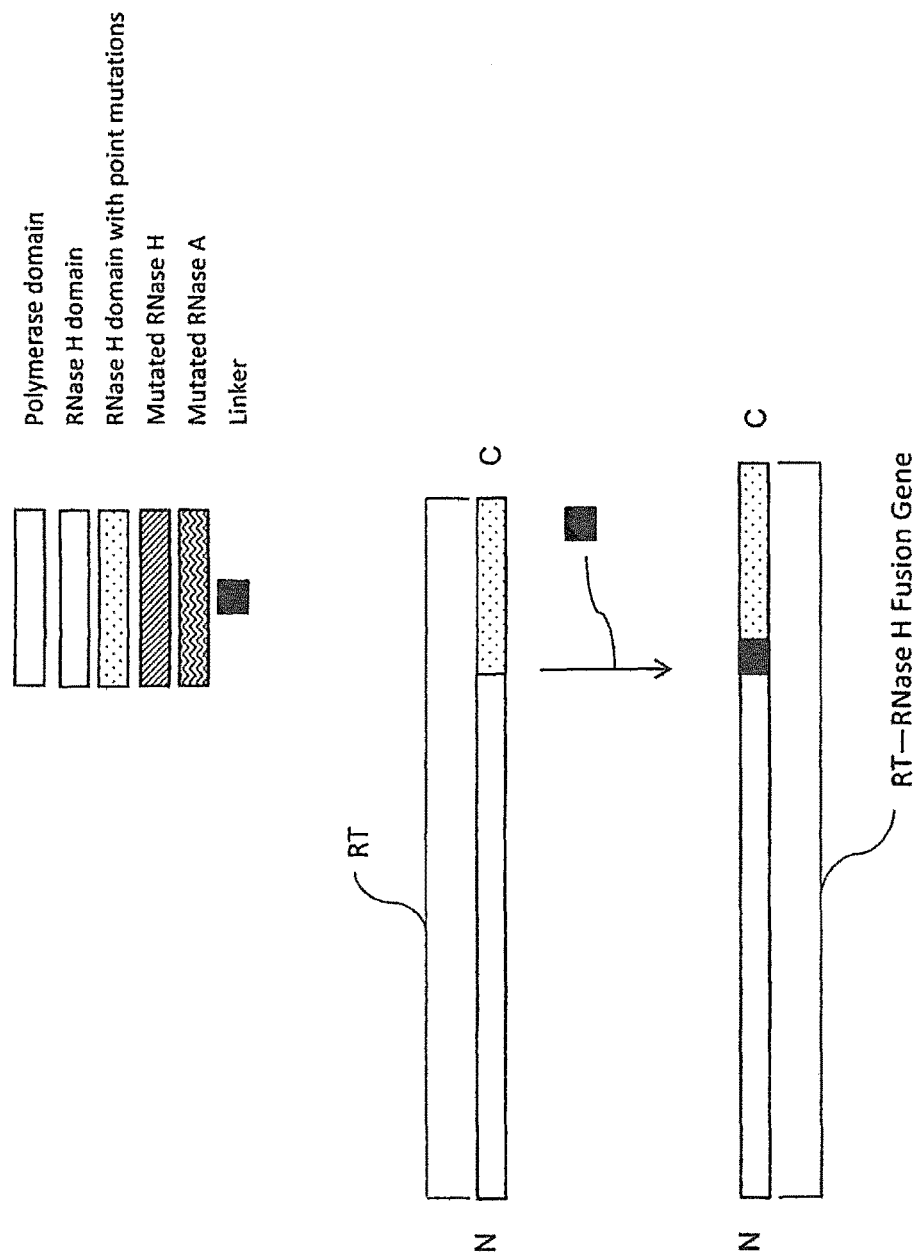
FIG. 1B illustrates a transition from an RT with point mutations to a linker-bridged gene fusion RT according to the present invention, wherein in frame N-terminal polymerase domain and in frame C-terminal RNase H domain are fused by a linker.

In a certain embodiment, the invention provides for a composition of a gene or domain fusion RT using a linker, wherein the composition comprises an in frame N-terminal polymerase domain and an in frame C-terminal RNase H domain that are joined by a linker consisting of 4-30 amino acids. In one embodiment, the RNase H domain is unmodified. An example is shown in FIG. 1A. In another embodiment, the RNase H domain is genetically engineered by point mutations. An example is shown in FIG. 1B.

Figure 2A:
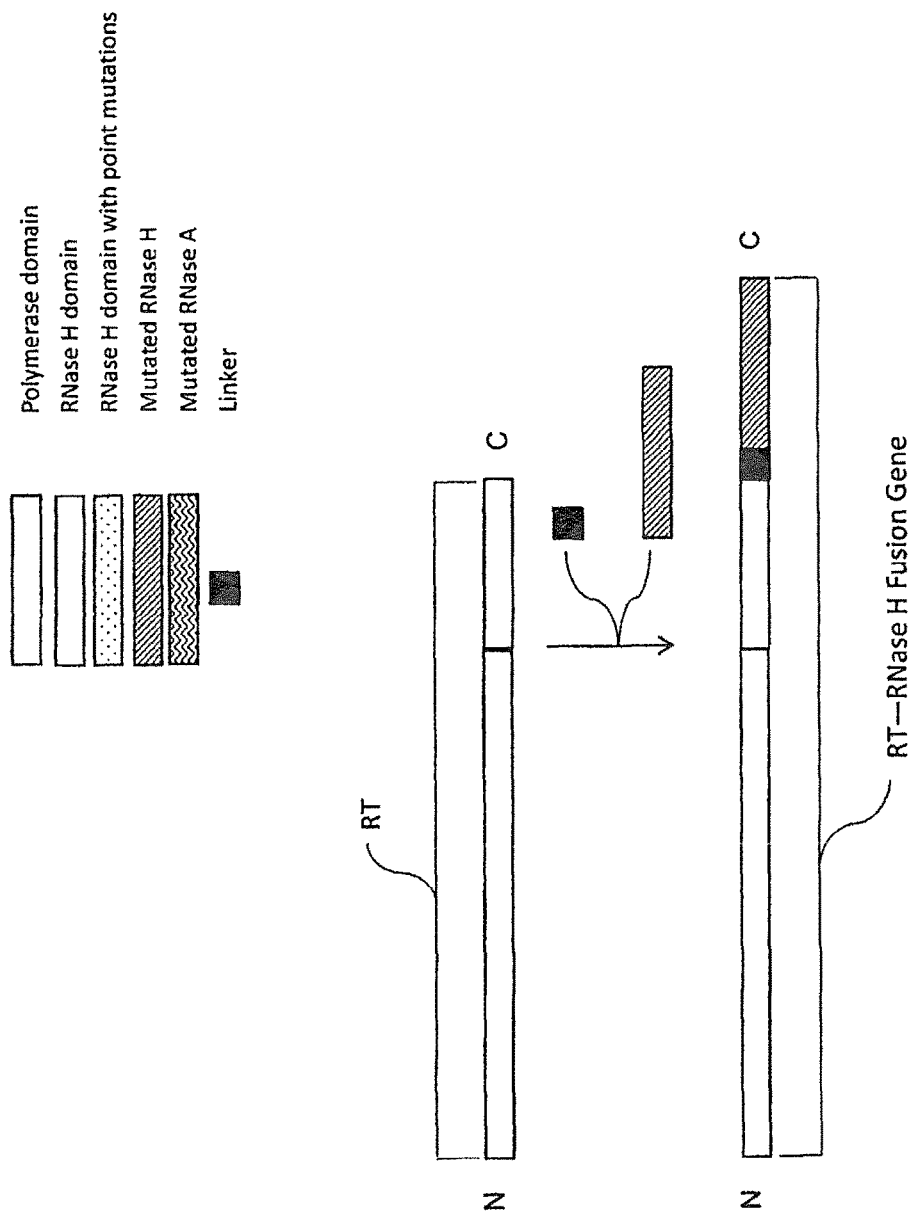
FIG. 2A illustrates a transition from an unmodified RT to a linker-bridged gene fusion RT according to the present invention, wherein a mutated RNase H is C-terminally joined by a linker to the unmodified RT.
Figure 2B:
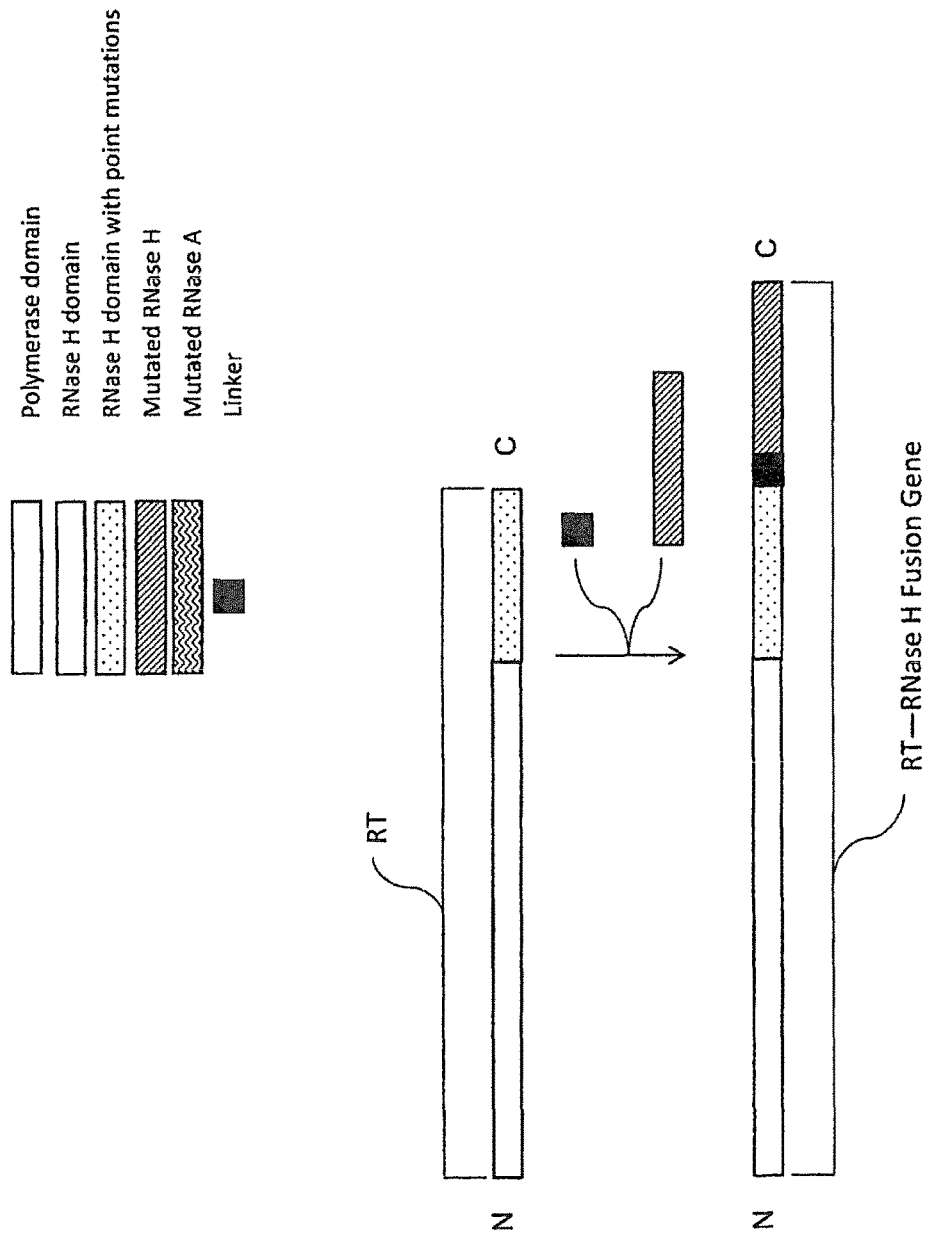
FIG. 2B illustrates a transition from an RT with point mutations to a linker-bridged gene fusion RT according to the present invention, wherein a mutated RNase H is C-terminally joined by a linker to the RT with point mutations.

In a certain embodiment, the invention also provides for a composition of a gene or domain fusion RT using a linker, wherein the composition comprises a gene or domain RT and a mutated RNase H that are C-terminally joined by a linker consisting of 4-30 amino acids. In one embodiment, the RNase H domain of the gene or domain RT is unmodified. An example is shown in FIG. 2A. In another embodiment, the RNase H domain of the gene or domain RT is genetically engineered by point mutations. An example is shown in FIG. 2B.

Figure 3:
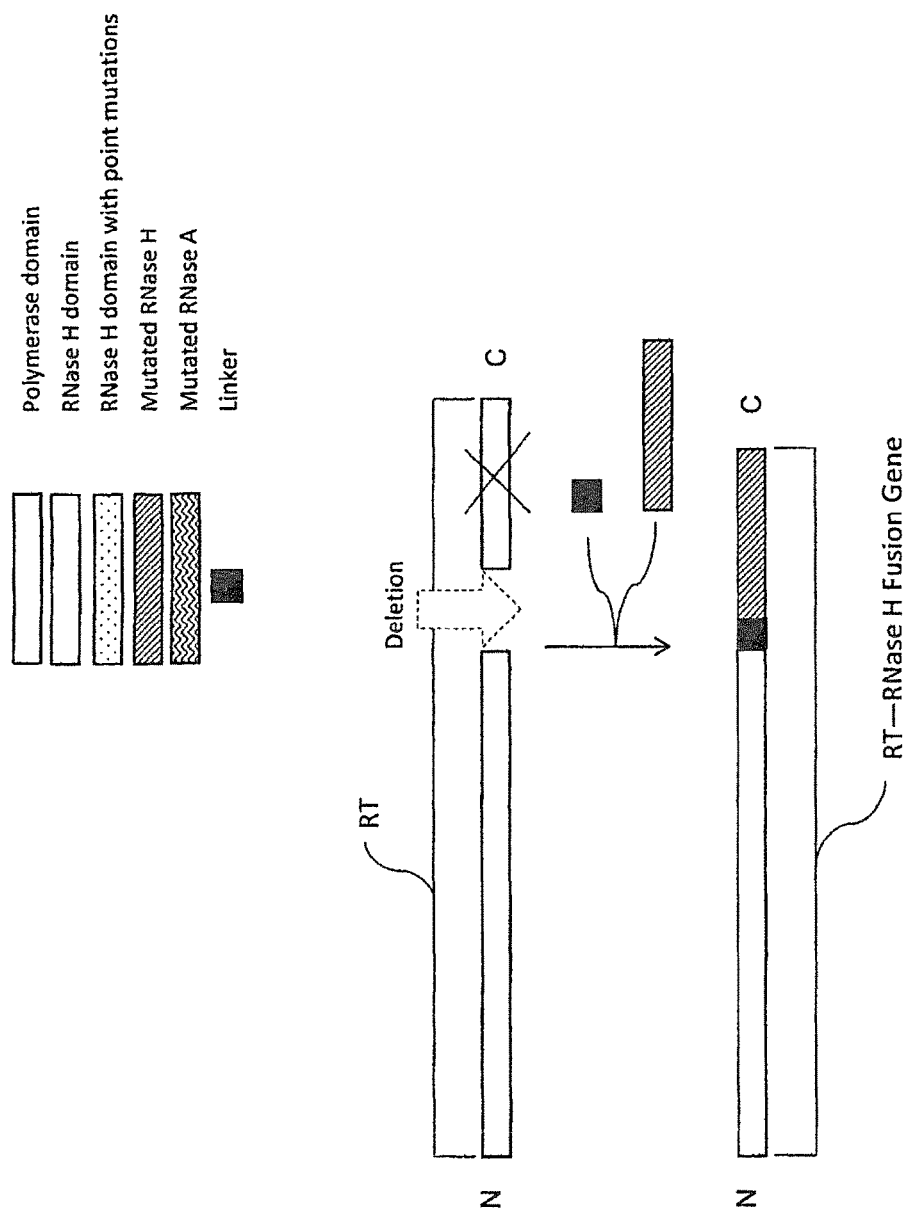
FIG. 3 illustrates a transition from an RT with RNase H domain deletion to a linker-bridged gene fusion RT according to another embodiment of the present invention, wherein a mutated RNase H is C-terminally joined by a linker to the RT with RNase H domain deletion.

In a certain embodiment, this invention also provides for a composition of a gene or domain fusion RT using a linker, wherein the composition comprises a gene or domain RT with C-terminal RNase H domain deletion and a mutated RNase H that are C-terminally joined by a linker consisting of 4-30 amino acids. An example is shown in FIG. 3.

Figure 4A:
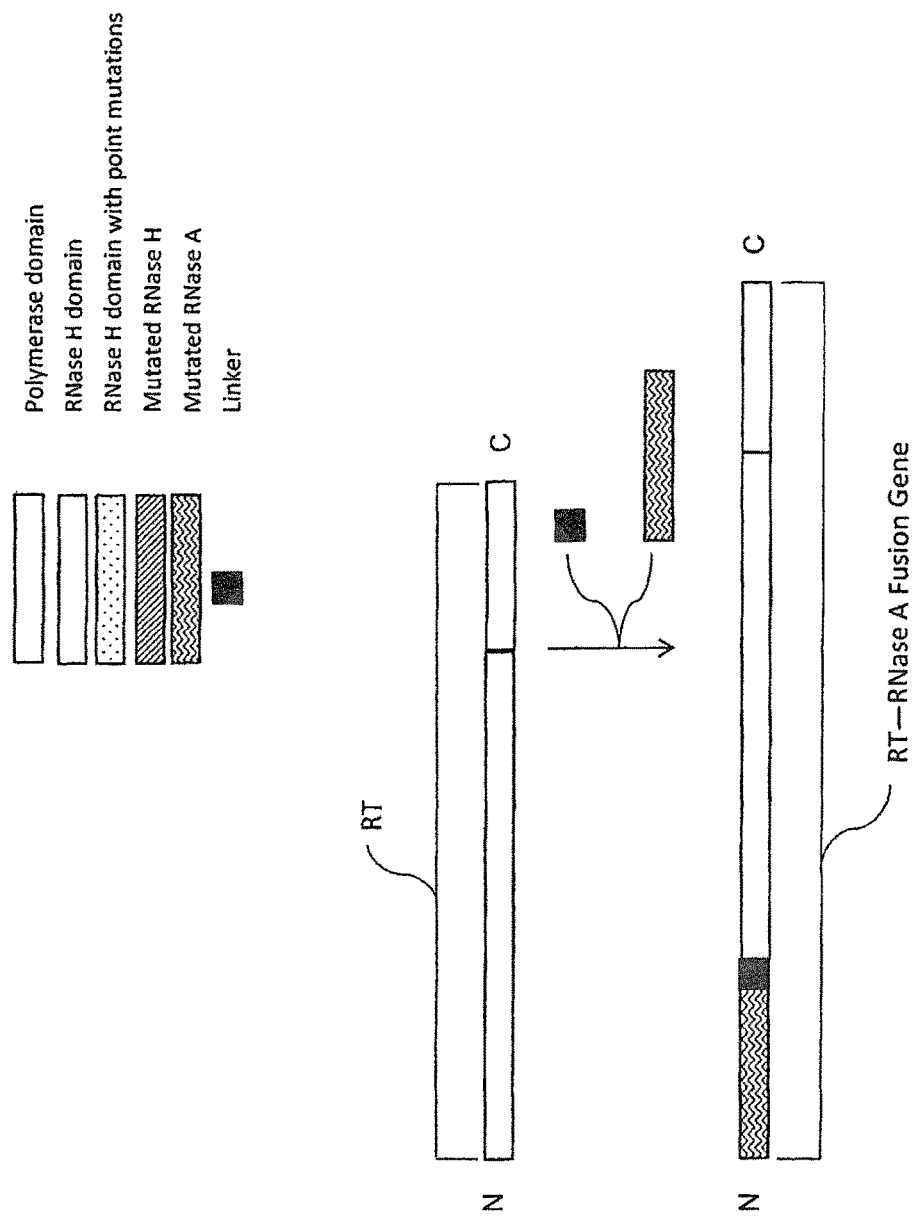
FIG. 4A illustrates a transition from an unmodified RT to a linker-bridged gene fusion RT according to still another embodiment of the present invention, wherein a mutated RNase A is N-terminally joined by a linker to the RT.
Figure 4B:
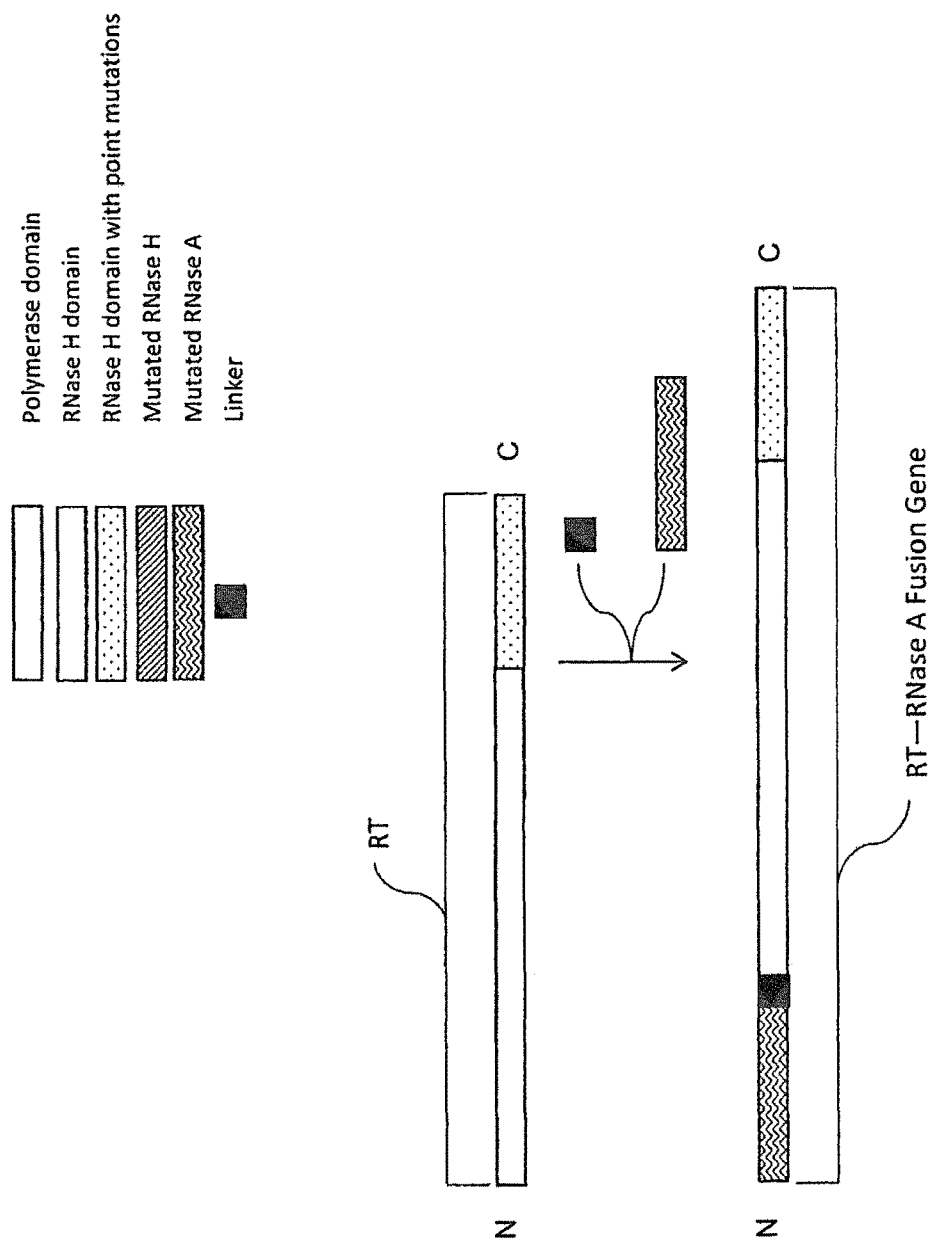
FIG. 4B illustrates a transition from an RT with point mutations to a linker-bridged gene fusion RT according to still another embodiment of the present invention, wherein a mutated RNase A is N-terminally joined by a linker to the RT with point mutations.

In a certain embodiment, this invention also provides for a composition of a gene or domain fusion RT using a linker, wherein the composition comprises a gene or domain RT and mutated RNase A that are N-terminally joined by a linker, consisting of 4-30 amino acids. In one embodiment, the RNase H domain of the gene or domain RT is unmodified. An example is shown in FIG. 4A. In another embodiment, the RNase H domain of the gene or domain RT is genetically engineered by point mutations. An example is shown in FIG. 4B.

Figure 5:
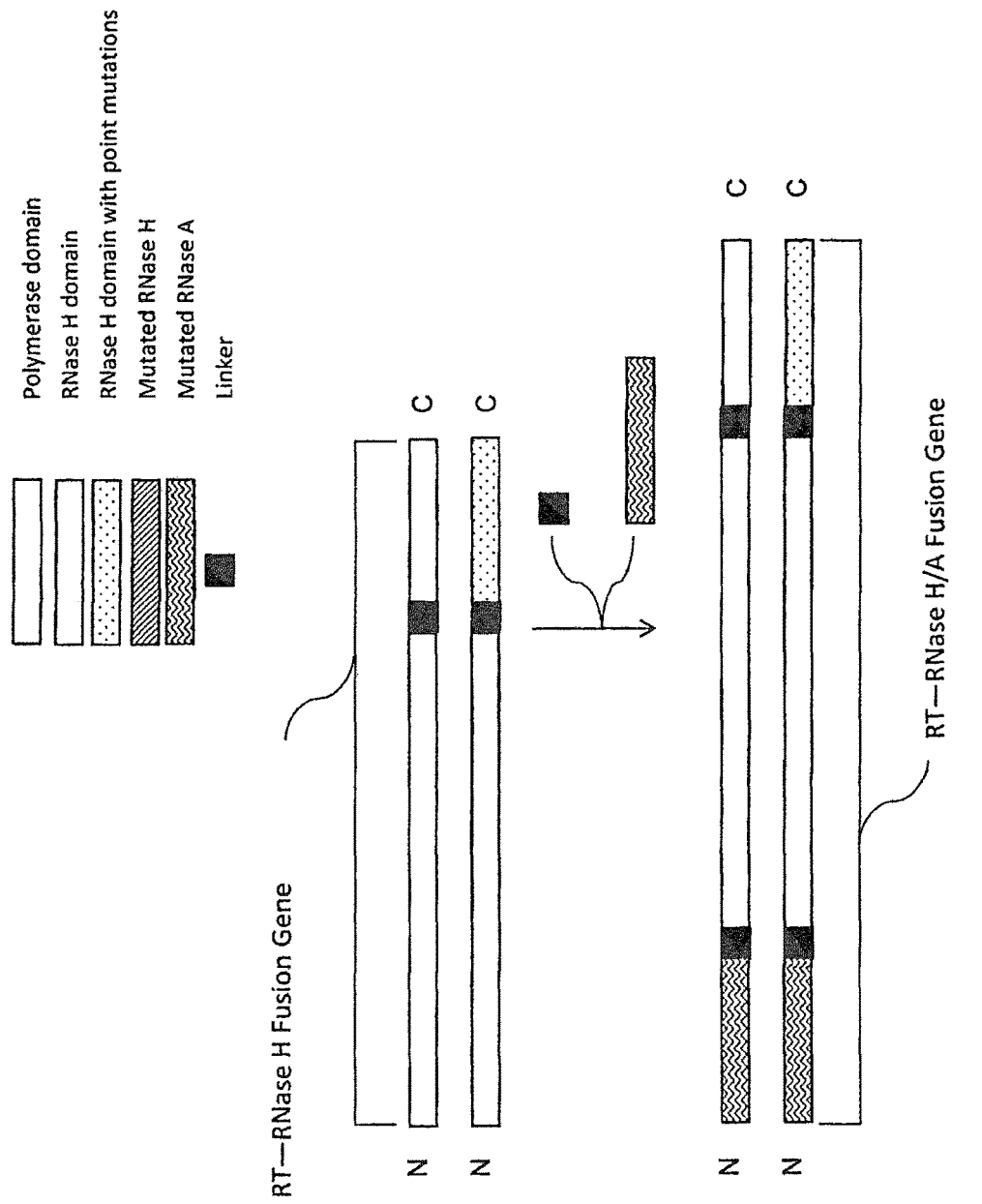
FIG. 5 illustrates a transition from a first linker-bridged gene fusion RT, wherein in frame N-terminal polymerase domain and in frame C-terminal RNase H domain, which is either unmodified or with point mutations, are joined by a linker, to a second linker-bridged gene fusion according to still another embodiment of the present invention, wherein a mutated RNase A is further N-terminally joined by another linker to the first linker-bridged gene fusion RT.

In a certain embodiment, this invention also provides for a composition of a gene or domain fusion RT using a linker, wherein the composition comprises an in frame N-terminal polymerase domain and an in frame C-terminal RNase H domain that are joined by a linker consisting of 4-30 amino acids. The composition of the embodiment further compromises a mutated RNase A which is N-terminally joined by another linker consisting of 4-30 amino acids. In one embodiment, the RNase H domain is unmodified. An example is shown in FIG. 5. In another embodiment, the RNase H domain is genetically engineered by point mutations. An example is also shown in FIG. 5.

Figure 6:
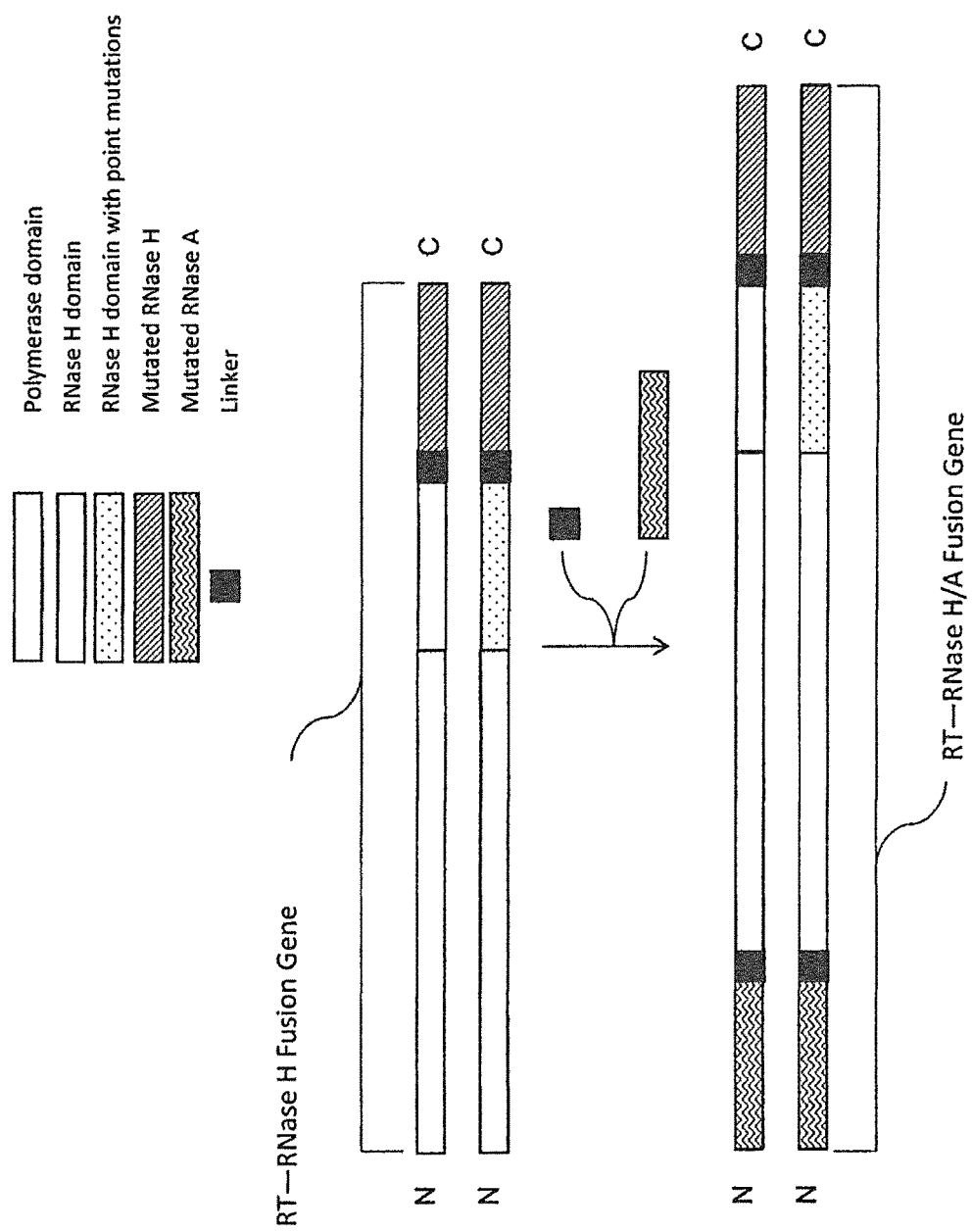
FIG. 6 illustrates a transition from a first linker-bridged gene fusion RT, wherein a mutated RNase H is C-terminally joined by a linker to an RT which has either unmodified RNase H domain or RNase H domain with point mutations, to a second linker-bridged gene fusion RT according to still another embodiment of the present invention, wherein a mutated RNase A is further N-terminally joined by another linker to the first linker-bridged gene fusion RT.

In a certain embodiment, this invention also provides for a composition of a gene or domain fusion RT using a linker, wherein the composition comprises a gene or domain RT and a mutated RNase H that are C-terminally joined by a linker consisting of 4-30 amino acids. The composition of the embodiment further compromises a mutated RNase A that is N-terminally joined by another linker consisting of 4-30 amino acids. In one embodiment, the RNase H domain of the gene or domain RT is unmodified. An example is shown in FIG. 6. In another embodiment, the RNase H domain of the gene or domain RT is genetically engineered by point mutations. An example is also shown in FIG. 6.

Figure 7:
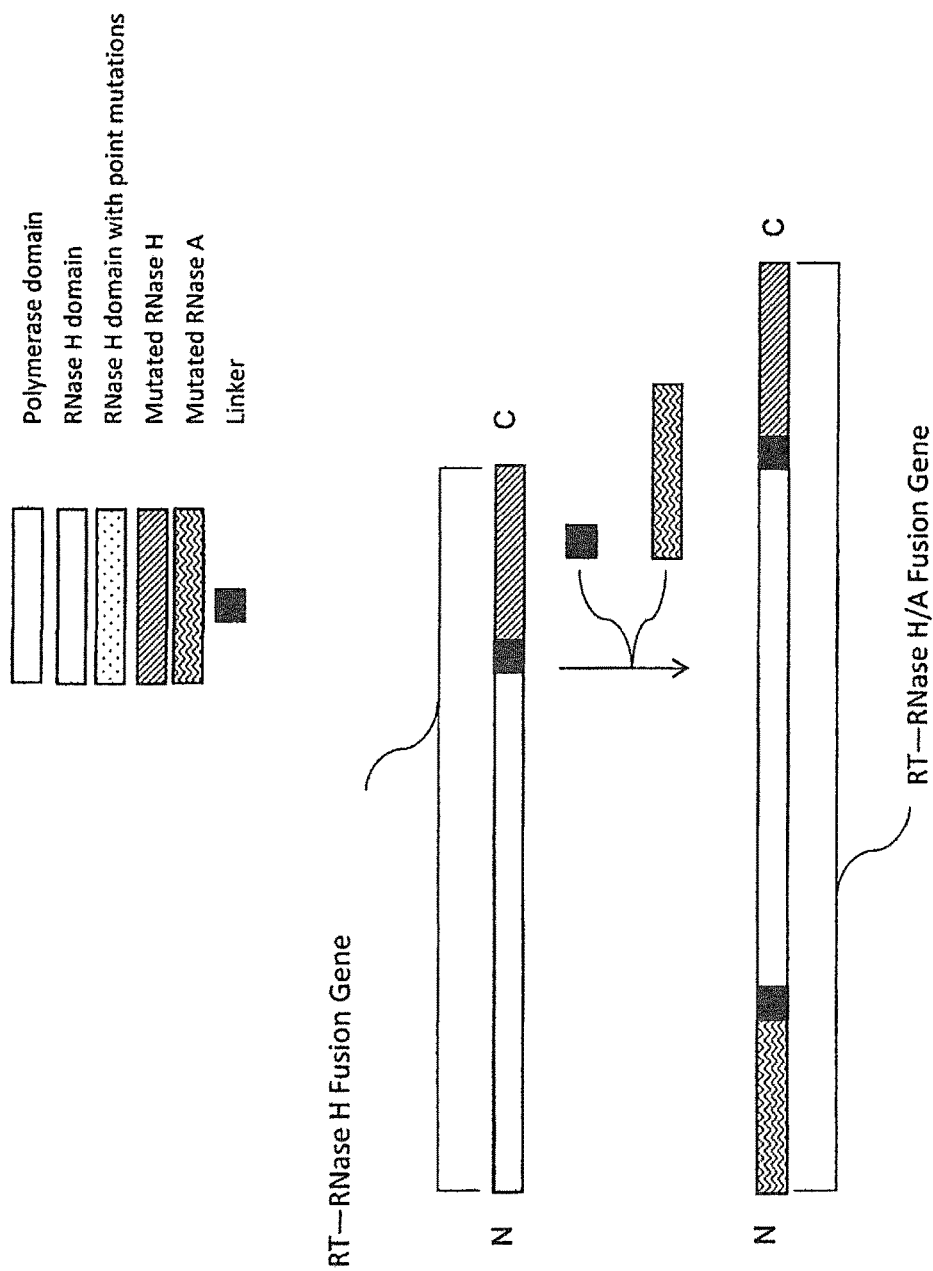
FIG. 7 illustrates a transition from a first linker-bridged gene fusion RT, wherein a mutated RNase H is C-terminally joined by a linker to an RT with RNase H domain deletion, to a second linker-bridged gene fusion RT according to still another embodiment of the present invention, wherein a mutated RNase A is further N-terminally joined by another linker to the first linker-bridged gene fusion RT.

In a certain embodiment, this invention also provides for a composition of a gene or domain fusion RT using a linker, wherein the composition comprises a gene or domain RT with RNase H domain deletion and a mutated RNase H that are joined by a linker consisting of 4-30 amino acids. The composition of the embodiment further compromises mutated RNase A that is N-terminally joined by another linker consisting of 4-30 amino acids. An example is shown in FIG. 7.

In some embodiments, the invention exhibits slow dissociation from RNA-primers and/or RNA-DNA hybrids due to its higher affinity to the RNA-primers and the RNA-DNA hybrids. In some embodiments, the invention further exhibits higher DNA yield, higher DNA quality, longer DNA chain extension and higher DNA replication fidelity in reverse transcription. In some embodiments, the invention also exhibits higher temperature performance which also contributes to high yields of quality full length cDNA with full gene representation.

Kits

The present invention also provides kits for carrying out cDNA synthesis such as cDNA yield and/or cDNA cloning, and/or RNA analysis such as RNA quantitation, RNA sequencing, gene expression profiling, transcription analysis and/or RNA quantitation.

In some embodiments, the kit may comprise reverse transcriptase(s), cofactor (magnesium), dNTPs, reaction buffer (Tris-chloride or Tris-acetate: pH 7.0-8.5), cationic ions (KCl and/or NaCl), reducing reagent (DTT or BME), enhancer, and stabilizer (detergents).

In some embodiments, the kit may comprise reverse transcriptase(s), cofactor (magnesium or manganese). dNTPs, reaction buffer (Tris-chloride or Tris-sulfate: pH 7.5-9.5), and cationic ions (KCl and/or NaCl), reducing reagent (DTT or BME), enhancer and stabilizer (detergents).

In other embodiments, the kit may comprise reverse transcriptase(s), cofactor (magnesium or manganese), dNTPs, reaction buffer (Tris-chloride or Tris-sulfate: pH 7.5-9.5), and cationic ions (KCl and/or NaCl), reducing reagent (DTT or BME), fluorescence dye (or syber dye), enhancer and stabilizer (detergents).

Data generation for the embodiment of FIG. 3
Constructed Following Two Fusion RT and Expressed, and Purified
(1) MMLV RT (deleted RNaseH domain)-Linker-RNaseH (*E. coli*) nucleotide sequence and amino acid sequence set forth in SEQ ID NO. 1 and ID NO. 2.
(2) MMLV RT (deleted RNaseH domain)-Linker-RNaseH (*Bacillus*) nucleotide sequence and amino acid sequence set forth in SEQ ID NO. 3 and SEQ ID NO. 4.
Gene and Amino Acid Sequence Information

```
(1) MMLV RT (deleted RNaseH domain)-Linker-RNaseH (E. coli):
2,025 bp
    1 M   T   L   N   I   E   D   E   H   R   L   H   E   T   S   K   E   P   D   V
    1 ATGACCCTGAACATCGAAGATGAACATCGTCTGCATGAAACCAGCAAAGAACCGGATGTG
    1         10        20        30        40        50
    1 TACTGGGACTTGTAGCTTCTACTTGTAGCAGACGTACTTTGGTCGTTTCTTGGCCTACAC 21 S   L   G   S   T   W   L   S   D   F   P   Q   A   W   A   E   T   G   G   M
   61 AGCCTGGGCAGCACCTGGCTGTCTGATTTTCCGCAGGCGTGGGCGGAAACCGGCGGTATG
   61         70        80        90       100       110
   61 TCGGACCCGTCGTGGACCGACAGACTAAAAGGCGTCCGCACCCGCCTTTGGCCGCCATAC 41 G   L   A   V   R   Q   A   P   L   I   I   P   L   K   A   T   S   T   P   V
  121 GGTCTGGCCGTTCGTCAGGCGCCGCTGATTATTCCGCTGAAAGCGACCAGCACCCCGGTG
  121        130       140       150       160       170
  121 CCAGACCGGCAAGCAGTCCGCGGCGACTAATAAGGCGACTTTCGCTGGTCGTGGGGCCAC 61 S   I   K   Q   Y   P   M   S   Q   E   A   R   L   G   I   K   P   H   I   Q
  181 AGCATTAAACAGTATCCGATGAGCCAGGAAGCGCGTCTGGGCATTAAACCGCATATTCAG
  181        190       200       210       220       230
  181 TCGTAATTTGTCATAGGCTACTCGGTCCTTCGCGCAGACCCGTAATTTGGCGTATAAGTC 81 R   L   L   D   Q   G   I   L   V   P   C   Q   S   P   W   N   T   P   L   L
  241 CGTCTGCTGGATCAGGGCATTCTGGTGCCGTGTCAGAGCCCGTGGAACACCCCGCTGCTG
  241        250       260       270       280       290
  241 GCAGACGACCTAGTCCCGTAAGACCACGGCACAGTCTCGGGCACCTTGTGGGGCGACGAC 101 P   V   K   K   P   G   T   N   D   Y   R   P   V   Q   D   L   R   E   V   N
  301 CCGGTGAAAAAACCGGGCACCAACGATTATCGTCCGGTGCAGGATCTGCGTGAAGTGAAC
  301        310       320       330       340       350
  301 GGCCACTTTTTTGGCCCGTGGTTGCTAATAGCAGGCCACGTCCTAGACGCACTTCACTTG 121 K   R   V   E   D   I   H   P   T   V   P   N   P   Y   N   L   L   S   G   L
  361 AAACGTGTGGAAGATATTCATCCGACCGTGCCGAATCCGTATAACCTGCTGTCTGGCCTG
  361        370       380       390       400       410
  361 TTTGCACACCTTCTATAAGTAGGCTGGCACGGCTTAGGCATATTGGACGACAGACCGGAC 141 P   P   S   H   Q   W   Y   T   V   L   D   L   K   D   A   F   F   C   L   R
  421 CCGCCGAGCCATCAGTGGTATACCGTGCTGGATCTGAAAGATGCGTTTTTTTGCCTGCGT
  421        430       440       450       460       470
  421 GGCGGCTCGGTAGTCACCATATGGCACGACCTAGACTTTCTACGCAAAAAAACGGACGCA 161 L   H   P   T   S   Q   P   L   F   A   F   E   W   R   D   P   E   M   G   I
```

-continued

```
481 CTGCATCCGACCAGCCAGCCGCTGTTTGCGTTTGAATGGCGTGATCCGGAAATGGGCATT
481          490       500       510       520       530
481 GACGTAGGCTGGTCGGTCGGCGACAAACGCAAACTTACCGCACTAGGCCTTTACCCGTAA

181 S  G  Q  L  T  W  T  R  L  P  Q  G  F  K  N  S  P  T  L  F
541 AGCGGCCAGCTGACCTGGACCCGTCTGCCGCAGGGCTTTAAAAACAGCCCGACCCTGTTT
541          550       560       570       580       590
541 TCGCCGGTCGACTGGACCTGGGCAGACGGCGTCCCGAAATTTTTGTCGGGCTGGGACAAA

201 D  E  A  L  H  R  D  L  A  D  F  R  I  Q  H  P  D  L  I  L
601 GATGAAGCGCTGCATCGTGATCTGGCCGATTTTCGTATTCAGCATCCGGATCTGATTCTG
601          610       620       630       640       650
601 CTACTTCGCGACGTAGCACTAGACCGGCTAAAAGCATAAGTCGTAGGCCTAGACTAAGAC

221 L  Q  Y  V  D  D  L  L  L  A  A  T  S  E  L  D  C  Q  Q  G
661 CTGCAGTATGTGGATGATCTGCTGCTGGCCGCGACCAGCGAACTGGATTGCCAGCAGGGC
661          670       680       690       700       710
661 GACGTCATACACCTACTAGACGACGACCGGCGCTGGTCGCTTGACCTAACGGTCGTCCCG

241 T  R  A  L  L  Q  T  L  G  N  L  G  Y  R  A  S  A  K  K  A
721 ACCCGTGCGCTGCTGCAGACCCTGGGCAACCTGGGCTATCGTGCGAGCGCGAAAAAAGCG
721          730       740       750       760       770
721 TGGGCACGCGACGACGTCTGGGACCCGTTGGACCCGATAGCACGCTCGCGCTTTTTTCGC

261 Q  I  C  Q  K  Q  V  K  Y  L  G  Y  L  L  K  E  G  Q  R  W
781 CAGATTTGCCAGAAACAGGTGAAATATCTGGGCTATCTGCTGAAAGAAGGCCAGCGTTGG
781          790       800       810       820       830
781 GTCTAAACGGTCTTTGTCCACTTTATAGACCCGATAGACGACTTTCTTCCGGTCGCAACC

281 L  T  E  A  R  K  E  T  V  M  G  Q  P  T  P  K  T  P  R  Q
841 CTGACCGAAGCGCGTAAAGAAACCGTGATGGGCCAGCCGACCCCGAAAACCCCGCGTCAG
841          850       860       870       880       890
841 GACTGGCTTCGCGCATTTCTTTGGCACTACCCGGTCGGCTGGGGCTTTTGGGGCGCAGTC

301 L  R  E  F  L  G  T  A  G  F  C  R  L  W  I  P  G  F  A  E
901 CTGCGTGAATTTCTGGGCACCGCGGGCTTTTGCCGTCTGTGGATTCCGGGCTTTGCGGAA
901          910       920       930       940       950
901 GACGCACTTAAAGACCCGTGGCGCCCGAAAACGGCAGACACCTAAGGCCCGAAACGCCTT

321 M  A  A  P  L  Y  P  L  T  K  T  G  T  L  F  N  W  G  P  D
961 ATGGCGGCGCCGCTGTATCCGCTGACCAAAACCGGCACCCTGTTTAACTGGGGTCCGGAT
961          970       980       990       1000      1010
961 TACCGCCGCGGCGACATAGGCGACTGGTTTTGGCCGTGGGACAAATTGACCCCAGGCCTA

341 Q  Q  K  A  Y  Q  E  I  K  Q  A  L  L  T  A  P  A  L  G  L
1021 CAGCAGAAAGCGTATCAGGAAATTAAACAGGCGCTGCTGACCGCGCCGGCGCTGGGTCTG
1021         1030      1040      1050      1060      1070
1021 GTCGTCTTTCGCATAGTCCTTTAATTTGTCCGCGACGACTGGCGCGGCCGCGACCCAGAC

361 P  D  L  T  K  P  F  E  L  F  V  D  E  K  Q  G  Y  A  K  G
1081 CCGGATCTGACCAAACCGTTTGAACTGTTCGTGGATGAAAAACAGGGCTATGCGAAAGGC
1081         1090      1100      1110      1120      1130
1081 GGCCTAGACTGGTTTGGCAAACTTGACAAGCACCTACTTTTTGTCCCGATACGCTTTCCG

381 V  L  T  Q  K  L  G  P  W  R  R  P  V  A  Y  L  S  K  K  L
1141 GTGCTGACCCAGAAACTGGGCCCGTGGCGTCGTCCGGTTGCGTATCTGAGCAAAAAACTG
1141         1150      1160      1170      1180      1190
1141 CACGACTGGGTCTTTGACCCGGGCACCGCAGCAGGCCAACGCATAGACTCGTTTTTTGAC

401 D  P  V  A  A  G  W  P  P  C  L  R  M  V  A  A  I  A  V  L
1201 GATCCGGTTGCGGCGGGTTGGCCGCCGTGTCTGCGCATGGTTGCGGCGATTGCGGTGCTG
1201         1210      1220      1230      1240      1250
1201 CTAGGCCAACGCCGCCCAACCGGCGGCACAGACGCGTACCAACGCCGCTAACGCCACGAC

421 T  K  D  A  G  K  L  T  M  G  Q  P  L  V  I  L  A  P  H  A
1261 ACCAAAGATGCGGGCAAACTGACCATGGGCCAGCCGCTGGTGATTCTGGCCCCGCATGCA
1261         1270      1280      1290      1300      1310
1261 TGGTTTCTACGCCCGTTTGACTGGTACCCGGTCGGCGACCACTAAGACCGGGCGTACGT

441 V  E  A  L  V  K  Q  P  P  D  R  W  L  S  N  A  R  M  T  H
1321 GTGGAAGCGCTGGTGAAACAGCCGCCGGATCGTTGGCTGTCTAACGCGCGTATGACCCAT
1321         1330      1340      1350      1360      1370
1321 CACCTTCGCGACCACTTTGTCGGCGGCCTAGCAACCGACAGATTGCGCGCATACTGGGTA

461 Y  Q  A  L  L  L  D  T  D  R  V  Q  F  G  P  V  V  A  L  N
1381 TATCAGGCCCTGCTGCTGGATACCGATCGTGTGCAGTTTGGCCCGGTGGTGGCGCTGAAT
1381         1390      1400      1410      1420      1430
1381 ATAGTCCGGGACGACGACCTATGGCTAGCACACGTCAAACCGGGCCACCACCGCGACTTA

481 P  A  T  L  L  P  L  P  E  E  G  L  Q  H  N  C  L  D  I  L
```

```
1441 CCGGCGACCCTGCTGCCGCTGCCGGAAGAAGGCCTGCAGCATAACTGCCTGGATATCCTG
1441      1450      1460      1470      1480      1490
1441 GGCCGCTGGGACGACGGCGACGGCCTTCTTCCGGACGTCGTATTGACGGACCTATAGGAC

501 A   E   A   H   G   T   R   P   D   L   T   D   Q   S   A   A   G   V   G   M
1501 GCCGAAGCGCATGGCACCCGTCCGGATCTGACCGATCAGAGCGCGGCGGGCGTGGGCATG
1501      1510      1520      1530      1540      1550
1501 CGGCTTCGCGTACCGTGGGCAGGCCTAGACTGGCTAGTCTCGCGCCGCCCGCACCCGTAC

521 L   K   Q   V   E   I   F   T   N   G   S   C   L   G   N   P   G   P   G   G
1561 CTGAAACAGGTGGAAATTTTTACCAACGGCAGCTGCCTGGGCAACCCGGGCCCGGGCGGC
1561      1570      1580      1590      1600      1610
1561 GACTTTGTCCACCTTTAAAAATGGTTGCCGTCGACGGACCCGTTGGGCCCGGGCCCGCCG

541 Y   G   A   I   L   R   Y   R   G   R   E   K   T   F   S   A   G   Y   T   R
1621 TATGGCGCGATTCTGCGCTATCGCGGCCGCGAAAAAACCTTTAGCGCGGGCTATACCCGC
1621      1630      1640      1650      1660      1670
1621 ATACCGCGCTAAGACGCGATAGCGCCGGCGCTTTTTTGGAAATCGCGCCCGATATGGGCG

561 T   T   N   N   R   M   Q   L   M   A   A   I   V   A   L   E   A   L   K   E
1681 ACCACCAACAACCGCATGCAGCTGATGGCGGCGATTGTGGCGCTGGAAGCGCTGAAAGAA
1681      1690      1700      1710      1720      1730
1681 TGGTGGTTGTTGGCGTACGTCGACTACCGCCGCTAACACCGCGACCTTCGCGACTTTCTT

581 H   C   E   V   I   L   S   T   N   S   Q   Y   V   R   Q   G   I   T   Q   W
1741 CATTGCGAAGTGATTCTGAGCACCAACAGCCAGTATGTGCGCCAGGGCATTACCCAGTGG
1741      1750      1760      1770      1780      1790
1741 GTAACGCTTCACTAAGACTCGTGGTTGTCGGTCATACACGCGGTCCCGTAATGGGTCACC

601 I   H   N   W   K   K   R   G   W   K   T   A   D   K   K   P   V   K   N   V
1801 ATTCATAACTGGAAAAAACGCGGCTGGAAAACCGCGGATAAAAAACCGGTGAAAAACGTG
1801      1810      1820      1830      1840      1850
1801 TAAGTATTGACCTTTTTTGCGCCGACCTTTTGGCGCCTATTTTTTGGCCACTTTTTGCAC

621 D   L   W   Q   R   L   D   A   A   L   G   Q   H   Q   I   K   W   E   W   V
1861 GATCTGTGGCAGCGCCTGGATGCGGCGCTGGGCCAGCATCAGATTAAATGGGAATGGGTG
1861      1870      1880      1890      1900      1910
1861 CTAGACACCGTCGCGGACCTACGCCGCGACCCGGTCGTAGTCTAATTTACCCTTACCCAC

641 K   G   H   A   G   H   P   E   N   E   R   C   D   E   L   A   R   A   A   A
1921 AAAGGCCATGCGGGCCATCCGGAAAACGAACGCTGCGATGAACTGGCGCGCGCGGCGGCG
1921      1930      1940      1950      1960      1970
1921 TTTCCGGTACGCCCGGTAGGCCTTTTGCTTGCGACGCTACTTGACCGCGCGCGCCGCCGC

661 M   N   P   T   L   E   D   T   G   Y   Q   V   E   V   *
1981 ATGAACCCGACCCTGGAAGATACCGGCTATCAGGTGGAAGTGTAA
1981      1990      2000      2010      2020
1981 TACTTGGGCTGGGACCTTCTATGGCCGATAGTCCACCTTCACATT (2) MMLV RT (deleted RNaseH domain)-Linker-RNaseH
(Bacillus): 1,974 bp, set forth in SEQ ID NO. 3 and 4.
   1 M   T   L   N   I   E   D   E   H   R   L   H   E   T   S   K   E   P   D   V
   1 ATGACCCTGAACATCGAAGATGAACATCGTCTGCATGAAACCAGCAAAGAACCGGATGTG
   1        10        20        30        40        50
   1 TACTGGGACTTGTAGCTTCTACTTGTAGCAGACGTACTTTGGTCGTTTCTTGGCCTACAC 21 S   L   G   S   T   W   L   S   D   F   P   Q   A   W   A   E   T   G   G   M
  61 AGCCTGGGCAGCACCTGGCTGTCTGATTTTCCGCAGGCGTGGGCGGAAACCGGCGGTATG
  61        70        80        90       100       110
  61 TCGGACCCGTCGTGGACCGACAGACTAAAAGGCGTCCGCACCCGCCTTTGGCCGCCATAC 41 G   L   A   V   R   Q   A   P   L   I   I   P   L   K   A   T   S   T   P   V
 121 GGTCTGGCCGTTCGTCAGGCGCCGCTGATTATTCCGCTGAAAGCGACCAGCACCCCGGTG
 121       130       140       150       160       170
 121 CCAGACCGGCAAGCAGTCCGCGGCGACTAATAAGGCGACTTTCGCTGGTCGTGGGGCCAC 61 S   I   K   Q   Y   P   M   S   Q   E   A   R   L   G   I   K   P   H   I   Q
 181 AGCATTAAACAGTATCCGATGAGCCAGGAAGCGCGTCTGGGCATTAAACCGCATATTCAG
 181       190       200       210       220       230
 181 TCGTAATTTGTCATAGGCTACTCGGTCCTTCGCGCAGACCCGTAATTTGGCGTATAAGTC 81 R   L   L   D   Q   G   I   L   V   P   C   Q   S   P   W   N   T   P   L   L
 241 CGTCTGCTGGATCAGGGCATTCTGGTGCCGTGTCAGAGCCCGTGGAACACCCCGCTGCTG
 241       250       260       270       280       290
 241 GCAGACGACCTAGTCCCGTAAGACCACGGCACAGTCTCGGGCACCTTGTGGGGCGACGAC 101 P   V   K   K   P   G   T   N   D   Y   R   P   V   Q   D   L   R   E   V   N
 301 CCGGTGAAAAAACCGGGCACCAACGATTATCGTCCGGTGCAGGATCTGCGTGAAGTGAAC
 301       310       320       330       340       350
 301 GGCCACTTTTTTGGCCCGTGGTTGCTAATAGCAGGCCACGTCCTAGACGCACTTCACTTG
```

```
                                          -continued

121 K   R   V   E   D   I   H   P   T   V   P   N   P   Y   N   L   L   S   G   L
361 AAACGTGTGGAAGATATTCATCCGACCGTGCCGAATCCGTATAACCTGCTGTCTGGCCTG
361         370       380       390       400       410
361 TTTGCACACCTTCTATAAGTAGGCTGGCACGGCTTAGGCATATTGGACGACAGACCGGAC

141 P   P   S   H   Q   W   Y   T   V   L   D   L   K   D   A   F   F   C   L   R
421 CCGCCGAGCCATCAGTGGTATACCGTGCTGGATCTGAAAGATGCGTTTTTTTGCCTGCGT
421         430       440       450       460       470
421 GGCGGCTCGGTAGTCACCATATGGCACGACCTAGACTTTCTACGCAAAAAAACGGACGCA

161 L   H   P   T   S   Q   P   L   F   A   F   E   W   R   D   P   E   M   G   I
481 CTGCATCCGACCAGCCAGCCGCTGTTTGCGTTTGAATGGCGTGATCCGGAAATGGGCATT
481         490       500       510       520       530
481 GACGTAGGCTGGTCGGTCGGCGACAAACGCAAACTTACCGCACTAGGCCTTTACCCGTAA

181 S   G   Q   L   T   W   T   R   L   P   Q   G   F   K   N   S   P   T   L   F
541 AGCGGCCAGCTGACCTGGACCCGTCTGCCGCAGGGCTTTAAAAACAGCCCGACCCTGTTT
541         550       560       570       580       590
541 TCGCCGGTCGACTGGACCTGGGCAGACGGCGTCCCGAAATTTTTGTCGGGCTGGGACAAA

201 D   E   A   L   H   R   D   L   A   D   F   R   I   Q   H   P   D   L   I   L
601 GATGAAGCGCTGCATCGTGATCTGGCCGATTTTCGTATTCAGCATCCGGATCTGATTCTG
601         610       620       630       640       650
601 CTACTTCGCGACGTAGCACTAGACCGGCTAAAAGCATAAGTCGTAGGCCTAGACTAAGAf

221 L   Q   Y   V   D   D   L   L   L   A   A   T   S   E   L   D   C   Q   Q   G
661 CTGCAGTATGTGGATGATCTGCTGCTGGCCGCGACCAGCGAACTGGATTGCCAGCAGGGC
661         670       680       690       700       710
661 GACGTCATACACCTACTAGACGACGACCGGCGCTGGTCGCTTGACCTAACGGTCGTCCCG

241 T   R   A   L   L   Q   T   L   G   N   L   G   Y   R   A   S   A   K   K   A
721 ACCCGTGCGCTGCTGCAGACCCTGGGCAACCTGGGCTATCGTGCGAGCGCGAAAAAAGCG
721         730       740       750       760       770
721 TGGGCACGCGACGACGTCTGGGACCCGTTGGACCCGATAGCACGCTCGCGCTTTTTTCGC

261 Q   I   C   Q   K   Q   V   K   Y   L   G   Y   L   L   K   E   G   Q   R   W
781 CAGATTTGCCAGAAACAGGTGAAATATCTGGGCTATCTGCTGAAAGAAGGCCAGCGTTGG
781         790       800       810       820       830
781 GTCTAAACGGTCTTTGTCCACTTTATAGACCCGATAGACGACTTTCTTCCGGTCGCAACC

281 L   T   E   A   R   K   E   T   V   M   G   Q   P   T   P   K   T   P   R   Q
841 CTGACCGAAGCGCGTAAAGAAACCGTGATGGGCCAGCCGACCCCGAAAACCCCGCGTCAG
841         850       860       870       880       890
841 GACTGGCTTCGCGCATTTCTTTGGCACTACCCGGTCGGCTGGGGCTTTTGGGGCGCAGTC

301 L   R   E   F   L   G   T   A   G   F   C   R   L   W   I   P   G   F   A   E
901 CTGCGTGAATTTCTGGGCACCGCGGGCTTTTGCCGTCTGTGGATTCCGGGCTTTGCGGAA
901         910       920       930       940       950
901 GACGCACTTAAAGACCCGTGGCGCCCGAAAACGGCAGACACCTAAGGCCCGAAACGCCTT

321 M   A   A   P   L   Y   P   L   T   K   T   G   T   L   F   N   W   G   P   D
961 ATGGCGGCGCCGCTGTATCCGCTGACCAAAACCGGCACCCTGTTTAACTGGGGTCCGGAT
961         970       980       990       1000      1010
961 TACCGCCGCGGCGACATAGGCGACTGGTTTTGGCCGTGGGACAAATTGACCCCAGGCCTA

341 Q   Q   K   A   Y   Q   E   I   K   Q   A   L   L   T   A   P   A   L   G   L
1021 CAGCAGAAAGCGTATCAGGAAATTAAACAGGCGCTGCTGACCGCGCCGGCGCTGGGTCTG
1021        1030      1040      1050      1060      1070
1021 GTCGTCTTTCGCATAGTCCTTTAATTTGTCCGCGACGACTGGCGCGGCCGCGACCCAGAC

361 P   D   L   T   K   P   F   E   L   F   V   D   E   K   Q   G   Y   A   K   G
1081 CCGGATCTGACCAAACCGTTTGAACTGTTCGTGGATGAAAAACAGGGCTATGCGAAAGGC
1081        1090      1100      1110      1120      1130
1081 GGCCTAGACTGGTTTGGCAAACTTGACAAGCACCTACTTTTTGTCCCGATACGCTTTCCG

381 V   L   T   Q   K   L   G   P   W   R   R   P   V   A   Y   L   S   K   K   L
1141 GTGCTGACCCAGAAACTGGGCCCGTGGCGTCGTCCGGTTGCGTATCTGAGCAAAAAACTG
1141        1150      1160      1170      1180      1190
1141 CACGACTGGGTCTTTGACCCGGGCACCGCAGCAGGCCAACGCATAGACTCGTTTTTTGAC

401 D   P   V   A   A   G   W   P   P   C   L   R   M   V   A   A   I   A   V   L
1201 GATCCGGTTGCGGCGGGTTGGCCGCCCGTGTCTGCGCATGGTTGCGGCGGATTGCGGTGCTG
1201        1210      1220      1230      1240      1250
1201 CTAGGCCAACGCCGCCCAACCGGCGGCACAGACGCGTACCAACGCCGCTAACGCCACGAC

421 T   K   D   A   G   K   L   T   M   G   Q   P   L   V   I   L   A   P   H   A
1261 ACCAAAGATGCGGGCAAACTGACCATGGGCCAGCCGCTGGTGATTCTGGCCCCGCATGCA
1261        1270      1280      1290      1300      1310
```

```
                                                          -continued
1261 TGGTTTCTACGCCCGTTTGACTGGTACCCGGTCGGCGACCACTAAGACCGGGGCGTACGT 441 V   E   A   L   V   K   Q   P   P   D   R   W   L   S   N   A   R   M   T   H
1321 GTGGAAGCGCTGGTGAAACAGCCGCCGGATCGTTGGCTGTCTAACGCGCGTATGACCCAT
1321         1330       1340       1350       1360       1370
1321 CACCTTCGCGACCACTTTGTCGGCGGCCTAGCAACCGACAGATTGCGCGCATACTGGGTA 461 Y   Q   A   L   L   L   D   T   D   R   V   Q   F   G   P   V   V   A   L   N
1381 TATCAGGCCCTGCTGCTGGATACCGATCGTGTGCAGTTTGGCCCGGTGGTGGCGCTGAAT
1381         1390       1400       1410       1420       1430
1381 ATAGTCCGGGACGACGACCTATGGCTAGCACACGTCAAACCGGGCCACCACCGCGACTTA 481 P   A   T   L   L   P   L   P   E   E   G   L   Q   H   N   C   L   D   I   L
1441 CCGGCGACCCTGCTGCCGCTGCCGGAAGAAGGCCTGCAGCATAACTGCCTGGATATCCTG
1441         1450       1460       1470       1480       1490
1441 GGCCGCTGGGACGACGGCGACGGCCTTCTTCCGGACGTCGTATTGACGGACCTATAGGAC 501 A   E   A   H   G   T   R   P   D   L   T   D   Q   S   A   A   G   V   G   A
1501 GCCGAAGCGCATGGCACCCGTCCGGATCTGACCGATCAGAGCGCGGCGGGCGTGGGCGCG
1501         1510       1520       1530       1540       1550
1501 CGGCTTCGCGTACCGTGGGCAGGCCTAGACTGGCTAGTCTCGCGCCGCCCGCACCCGCGC 521 K   E   E   I   I   W   E   S   L   S   V   D   V   G   S   Q   G   N   P   G
1561 AAAGAAGAAATTATTTGGGAAAGCCTGAGCGTGGATGTGGGCAGCCAGGGCAACCCGGGC
1561         1570       1580       1590       1600       1610
1561 TTTCTTCTTTAATAAACCCTTTCGGACTCGCACCTACACCCGTCGGTCCCGTTGGGCCCG 541 I   V   E   Y   K   G   V   D   T   K   T   G   E   V   L   F   E   R   E   P
1621 ATTGTGGAATATAAAGGCGTGGATACCAAAACCGGCGAAGTGCTGTTTGAACGCGAACCG
1621         1630       1640       1650       1660       1670
1621 TAACACCTTATATTTCCGCACCTATGGTTTTGGCCGCTTCACGACAAACTTGCGCTTGGC 561 I   P   I   G   T   N   N   M   G   Q   F   L   A   I   V   H   G   L   R   Y
1681 ATTCCGATTGGCACCAACAACATGGGCCAGTTTCTGGCGATTGTGCATGGCCTGCGCTAT
1681         1690       1700       1710       1720       1730
1681 TAAGGCTAACCGTGGTTGTTGTACCCGGTCAAAGACCGCTAACACGTACCGGACGCGATA 581 L   K   E   R   N   S   R   K   P   I   Y   S   N   S   Q   T   A   I   K   W
1741 CTGAAAGAACGCAACAGCCGCAAACCGATTTATAGCAACAGCCAGACCGCGATTAAATGG
1741         1750       1760       1770       1780       1790
1741 GACTTTCTTGCGTTGTCGGCGTTTGGCTAAATATCGTTGTCGGTCTGGCGCTAATTTACC 601 V   K   D   K   K   A   K   S   T   L   V   R   N   E   E   T   A   L   I   W
1801 GTGAAAGATAAAAAAGCGAAAAGCACCCTGGTGCGCAACGAAGAAACCGCGCTGATTTGG
1801         1810       1820       1830       1840       1850
1801 CACTTTCTATTTTTTCGCTTTTCGTGGGACCACGCGTTGCTTCTTTGGCGCGACTAAACC 621 K   L   V   D   E   A   E   E   W   L   N   T   H   T   Y   E   T   P   I   L
1861 AAACTGGTGGATGAAGCGGAAGAATGGCTGAACACCCATACCTATGAAACCCCCGATTCTG
1861         1870       1880       1890       1900       1910
1861 TTTGACCACCTACTTCGCCTTCTTACCGACTTGTGGGTATGGATACTTTGGGGCTAAGAC 641 K   W   Q   T   D   K   W   G   E   I   K   A   D   Y   G   R   K   *
1921 AAATGGCAGACCGATAAATGGGGCGAAATTAAAGCGGATTATGGCCGCAAATAA
1921         1930       1940       1950       1960       1970
1921 TTTACCGTCTGGCTATTTACCCCGCTTTAATTTCGCCTAATACCGGCGTTTATT
```

Figures 1, 3:
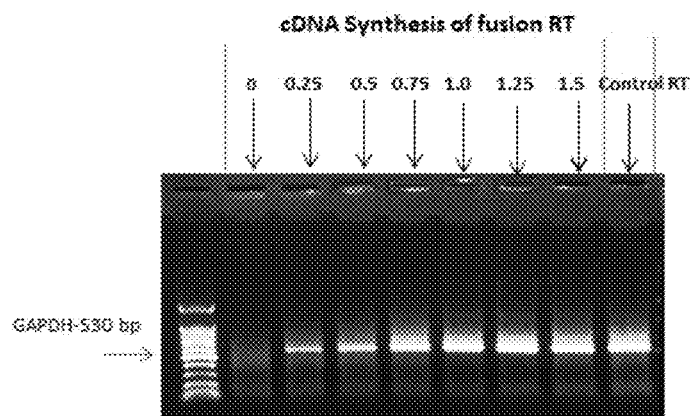
Figures 2, 3:
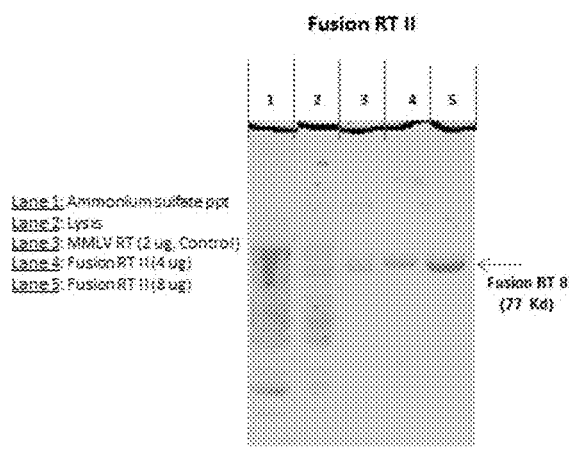
Figure 3:
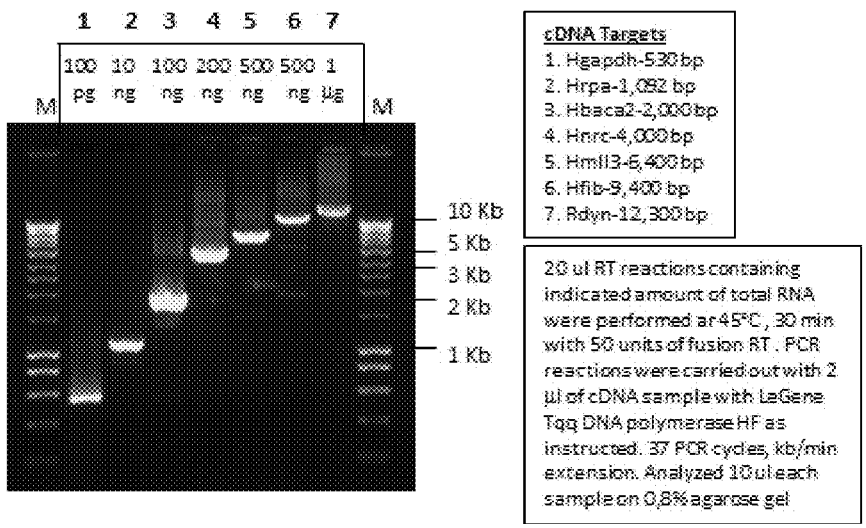
Figures 3, 4:
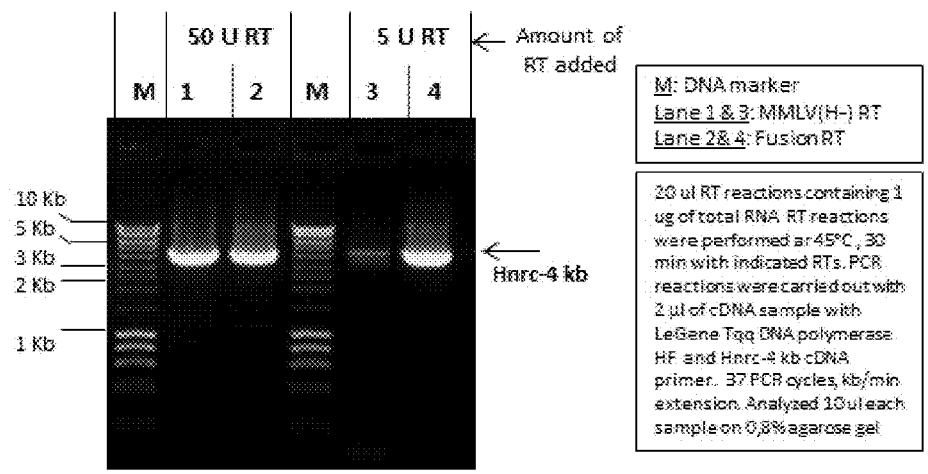

Cloned Genes, Expressed, Purified Proteins and Examined Reverse Transcriptase Activities Cloned the above fusion RT genes into T7 promotor expression vector. Grow cells in LB broth at 37 degree to OD600 1.0, IPTG induced (1 mM final) and grow for 2 hours and harvest cells by centrifuge 12,000 rpm 10 minutes. Lysed cells by sonication, and pass through P11 column, Heparine sepharose column, and SP Sepharose column. Dialyzed purified proteins and stored at −80° C. freezer until use.

cDNA Synthesis Activity of Fusion RTs a. Fusion RT 1 (*E. coli* RNaseH fusion RT): Observed efficient cDNA synthesis activity (FIG. 3-1).

b. Fusion RT 1I (*Bacillus* RNaseH fusion RT): Purified fusion RT near homogeneity (FIG. 3-2). Observed efficient cDNA synthesis activity with up to 12.3 kb mRNA targets with this purified fusion RT (FIG. 3-3). Demonstrated full cDNA synthesis capacity with only 5 units of fusion RT (FIG. 3-4). This indicates that the cloned fusion RT is highly processive.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A fusion reverse transcriptase, comprising:

a polymerase domain;

an RNase H domain; and a linker, comprising 4-30 amino acids;

wherein the fusion reverse transcriptase amino acid sequence is as set forth in SEQ ID NO. 4.

* * * * *

SEQUENCE LISTING

```
<160> NUMBER OF SEQ ID NOS: 9

<210> SEQ ID NO 1
<211> LENGTH: 2025
<212> TYPE: DNA
<213> ORGANISM: Artificial Sequence
<220> FEATURE:
<223> OTHER INFORMATION: Fusion Reverse Trnascriptase (MMLV RTwith RNase
      H domain deleted-Linker-RNaseH (E.Coli))
<220> FEATURE:
<221> NAME/KEY: CDS
<222> LOCATION: (1)..(2025)

<400> SEQUENCE: 1 atg acc ctg aac atc gaa gat gaa cat cgt ctg cat gaa acc agc aaa        48
Met Thr Leu Asn Ile Glu Asp Glu His Arg Leu His Glu Thr Ser Lys
1               5                   10                  15 gaa ccg gat gtg agc ctg ggc agc acc tgg ctg tct gat ttt ccg cag        96
Glu Pro Asp Val Ser Leu Gly Ser Thr Trp Leu Ser Asp Phe Pro Gln
            20                  25                  30 gcg tgg gcg gaa acc ggc ggt atg ggt ctg gcc gtt cgt cag gcg ccg       144
Ala Trp Ala Glu Thr Gly Gly Met Gly Leu Ala Val Arg Gln Ala Pro
        35                  40                  45 ctg att att ccg ctg aaa gcg acc agc acc ccg gtg agc att aaa cag       192
Leu Ile Ile Pro Leu Lys Ala Thr Ser Thr Pro Val Ser Ile Lys Gln
    50                  55                  60 tat ccg atg agc cag gaa gcg cgt ctg ggc att aaa ccg cat att cag       240
Tyr Pro Met Ser Gln Glu Ala Arg Leu Gly Ile Lys Pro His Ile Gln
65                  70                  75                  80 cgt ctg ctg gat cag ggc att ctg gtg ccg tgt cag agc ccg tgg aac       288
Arg Leu Leu Asp Gln Gly Ile Leu Val Pro Cys Gln Ser Pro Trp Asn
                85                  90                  95 acc ccg ctg ctg ccg gtg aaa aaa ccg ggc acc aac gat tat cgt ccg       336
Thr Pro Leu Leu Pro Val Lys Lys Pro Gly Thr Asn Asp Tyr Arg Pro
            100                 105                 110
```

```
                                                       -continued gtg cag gat ctg cgt gaa gtg aac aaa cgt gtg gaa gat att cat ccg    384
Val Gln Asp Leu Arg Glu Val Asn Lys Arg Val Glu Asp Ile His Pro
        115                 120                 125 acc gtg ccg aat ccg tat aac ctg ctg tct ggc ctg ccg ccg agc cat    432
Thr Val Pro Asn Pro Tyr Asn Leu Leu Ser Gly Leu Pro Pro Ser His
130                 135                 140 cag tgg tat acc gtg ctg gat ctg aaa gat gcg ttt ttt tgc ctg cgt    480
Gln Trp Tyr Thr Val Leu Asp Leu Lys Asp Ala Phe Phe Cys Leu Arg
145                 150                 155                 160 ctg cat ccg acc agc cag ccg ctg ttt gcg ttt gaa tgg cgt gat ccg    528
Leu His Pro Thr Ser Gln Pro Leu Phe Ala Phe Glu Trp Arg Asp Pro
                165                 170                 175 gaa atg ggc att agc ggc cag ctg acc tgg acc cgt ctg ccg cag ggc    576
Glu Met Gly Ile Ser Gly Gln Leu Thr Trp Thr Arg Leu Pro Gln Gly
            180                 185                 190 ttt aaa aac agc ccg acc ctg ttt gat gaa gcg ctg cat cgt gat ctg    624
Phe Lys Asn Ser Pro Thr Leu Phe Asp Glu Ala Leu His Arg Asp Leu
        195                 200                 205 gcc gat ttt cgt att cag cat ccg gat ctg att ctg ctg cag tat gtg    672
Ala Asp Phe Arg Ile Gln His Pro Asp Leu Ile Leu Leu Gln Tyr Val
    210                 215                 220 gat gat ctg ctg ctg gcc gcg acc agc gaa ctg gat tgc cag cag ggc    720
Asp Asp Leu Leu Leu Ala Ala Thr Ser Glu Leu Asp Cys Gln Gln Gly
225                 230                 235                 240 acc cgt gcg ctg ctg cag acc ctg ggc aac ctg ggc tat cgt gcg agc    768
Thr Arg Ala Leu Leu Gln Thr Leu Gly Asn Leu Gly Tyr Arg Ala Ser
                245                 250                 255 gcg aaa aaa gcg cag att tgc cag aaa cag gtg aaa tat ctg ggc tat    816
Ala Lys Lys Ala Gln Ile Cys Gln Lys Gln Val Lys Tyr Leu Gly Tyr
            260                 265                 270 ctg ctg aaa gaa ggc cag cgt tgg ctg acc gaa gcg cgt aaa gaa acc    864
Leu Leu Lys Glu Gly Gln Arg Trp Leu Thr Glu Ala Arg Lys Glu Thr
        275                 280                 285 gtg atg ggc cag ccg acc ccg aaa acc ccg cgt cag ctg cgt gaa ttt    912
Val Met Gly Gln Pro Thr Pro Lys Thr Pro Arg Gln Leu Arg Glu Phe
    290                 295                 300 ctg ggc acc gcg ggc ttt tgc cgt ctg tgg att ccg ggc ttt gcg gaa    960
Leu Gly Thr Ala Gly Phe Cys Arg Leu Trp Ile Pro Gly Phe Ala Glu
305                 310                 315                 320 atg gcg gcg ccg ctg tat ccg ctg acc aaa acc ggc acc ctg ttt aac   1008
Met Ala Ala Pro Leu Tyr Pro Leu Thr Lys Thr Gly Thr Leu Phe Asn
                325                 330                 335 tgg ggt ccg gat cag cag aaa gcg tat cag gaa att aaa cag gcg ctg   1056
Trp Gly Pro Asp Gln Gln Lys Ala Tyr Gln Glu Ile Lys Gln Ala Leu
            340                 345                 350 ctg acc gcg ccg gcg ctg ggt ctg ccg gat ctg acc aaa ccg ttt gaa   1104
Leu Thr Ala Pro Ala Leu Gly Leu Pro Asp Leu Thr Lys Pro Phe Glu
        355                 360                 365 ctg ttc gtg gat gaa aaa cag ggc tat gcg aaa ggc gtg ctg acc cag   1152
Leu Phe Val Asp Glu Lys Gln Gly Tyr Ala Lys Gly Val Leu Thr Gln
    370                 375                 380 aaa ctg ggc ccg tgg cgt cgt ccg gtt gcg tat ctg agc aaa aaa ctg   1200
Lys Leu Gly Pro Trp Arg Arg Pro Val Ala Tyr Leu Ser Lys Lys Leu
385                 390                 395                 400 gat ccg gtt gcg gcg ggt tgg ccg ccg tgt ctg cgc atg gtt gcg gcg   1248
Asp Pro Val Ala Ala Gly Trp Pro Pro Cys Leu Arg Met Val Ala Ala
                405                 410                 415 att gcg gtg ctg acc aaa gat gcg ggc aaa ctg acc atg ggc cag ccg   1296
Ile Ala Val Leu Thr Lys Asp Ala Gly Lys Leu Thr Met Gly Gln Pro
            420                 425                 430
```

```
ctg gtg att ctg gcc ccg cat gca gtg gaa gcg ctg gtg aaa cag ccg      1344
Leu Val Ile Leu Ala Pro His Ala Val Glu Ala Leu Val Lys Gln Pro
        435                 440                 445 ccg gat cgt tgg ctg tct aac gcg cgt atg acc cat tat cag gcc ctg      1392
Pro Asp Arg Trp Leu Ser Asn Ala Arg Met Thr His Tyr Gln Ala Leu
450                 455                 460 ctg ctg gat acc gat cgt gtg cag ttt ggc ccg gtg gtg gcg ctg aat      1440
Leu Leu Asp Thr Asp Arg Val Gln Phe Gly Pro Val Val Ala Leu Asn
465                 470                 475                 480 ccg gcg acc ctg ctg ccg ctg ccg gaa gaa ggc ctg cag cat aac tgc      1488
Pro Ala Thr Leu Leu Pro Leu Pro Glu Glu Gly Leu Gln His Asn Cys
                485                 490                 495 ctg gat atc ctg gcc gaa gcg cat ggc acc cgt ccg gat ctg acc gat      1536
Leu Asp Ile Leu Ala Glu Ala His Gly Thr Arg Pro Asp Leu Thr Asp
            500                 505                 510 cag agc gcg gcg ggc gtg ggc atg ctg aaa cag gtg gaa att ttt acc      1584
Gln Ser Ala Ala Gly Val Gly Met Leu Lys Gln Val Glu Ile Phe Thr
        515                 520                 525 aac ggc agc tgc ctg ggc aac ccg ggc ccg ggc ggc tat ggc gcg att      1632
Asn Gly Ser Cys Leu Gly Asn Pro Gly Pro Gly Gly Tyr Gly Ala Ile
530                 535                 540 ctg cgc tat cgc ggc cgc gaa aaa acc ttt agc gcg ggc tat acc cgc      1680
Leu Arg Tyr Arg Gly Arg Glu Lys Thr Phe Ser Ala Gly Tyr Thr Arg
545                 550                 555                 560 acc acc aac aac cgc atg cag ctg atg gcg gcg att gtg gcg ctg gaa      1728
Thr Thr Asn Asn Arg Met Gln Leu Met Ala Ala Ile Val Ala Leu Glu
                565                 570                 575 gcg ctg aaa gaa cat tgc gaa gtg att ctg agc acc aac agc cag tat      1776
Ala Leu Lys Glu His Cys Glu Val Ile Leu Ser Thr Asn Ser Gln Tyr
            580                 585                 590 gtg cgc cag ggc att acc cag tgg att cat aac tgg aaa aaa cgc ggc      1824
Val Arg Gln Gly Ile Thr Gln Trp Ile His Asn Trp Lys Lys Arg Gly
        595                 600                 605 tgg aaa acc gcg gat aaa aaa ccg gtg aaa aac gtg gat ctg tgg cag      1872
Trp Lys Thr Ala Asp Lys Lys Pro Val Lys Asn Val Asp Leu Trp Gln
610                 615                 620 cgc ctg gat gcg gcg ctg ggc cag cat cag att aaa tgg gaa tgg gtg      1920
Arg Leu Asp Ala Ala Leu Gly Gln His Gln Ile Lys Trp Glu Trp Val
625                 630                 635                 640 aaa ggc cat gcg ggc cat ccg gaa aac gaa cgc tgc gat gaa ctg gcg      1968
Lys Gly His Ala Gly His Pro Glu Asn Glu Arg Cys Asp Glu Leu Ala
                645                 650                 655 cgc gcg gcg gcg atg aac ccg acc ctg gaa gat acc ggc tat cag gtg      2016
Arg Ala Ala Ala Met Asn Pro Thr Leu Glu Asp Thr Gly Tyr Gln Val
            660                 665                 670 gaa gtg taa                                                          2025
Glu Val <210> SEQ ID NO 2
<211> LENGTH: 674
<212> TYPE: PRT
<213> ORGANISM: Artificial Sequence
<220> FEATURE:
<223> OTHER INFORMATION: Synthetic Construct

<400> SEQUENCE: 2

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30
```

-continued

```
Ala Trp Ala Glu Thr Gly Gly Met Gly Leu Ala Val Arg Gln Ala Pro
         35                  40                  45

Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
             100                 105                 110

Val Gln Asp Leu Arg Glu Val Asn Lys Arg Val Glu Asp Ile His Pro
         115                 120                 125

Thr Val Pro Asn Pro Tyr Asn Leu Leu Ser Gly Leu Pro Pro Ser His
     130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                 165                 170                 175

Glu Met Gly Ile Ser Gly Gln Leu Thr Trp Thr Arg Leu Pro Gln Gly
             180                 185                 190

Phe Lys Asn Ser Pro Thr Leu Phe Asp Glu Ala Leu His Arg Asp Leu
         195                 200                 205

Ala Asp Phe Arg Ile Gln His Pro Asp Leu Ile Leu Leu Gln Tyr Val
     210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                 245                 250                 255

Ala Lys Lys Ala Gln Ile Cys Gln Lys Gln Val Lys Tyr Leu Gly Tyr
             260                 265                 270

Leu Leu Lys Glu Gly Gln Arg Trp Leu Thr Glu Ala Arg Lys Glu Thr
         275                 280                 285

Val Met Gly Gln Pro Thr Pro Lys Thr Pro Arg Gln Leu Arg Glu Phe
     290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                 325                 330                 335

Trp Gly Pro Asp Gln Gln Lys Ala Tyr Gln Glu Ile Lys Gln Ala Leu
             340                 345                 350

Leu Thr Ala Pro Ala Leu Gly Leu Pro Asp Leu Thr Lys Pro Phe Glu
         355                 360                 365

Leu Phe Val Asp Glu Lys Gln Gly Tyr Ala Lys Gly Val Leu Thr Gln
     370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                 405                 410                 415

Ile Ala Val Leu Thr Lys Asp Ala Gly Lys Leu Thr Met Gly Gln Pro
             420                 425                 430

Leu Val Ile Leu Ala Pro His Ala Val Glu Ala Leu Val Lys Gln Pro
         435                 440                 445
```

```
Pro Asp Arg Trp Leu Ser Asn Ala Arg Met Thr His Tyr Gln Ala Leu
    450             455                 460
Leu Leu Asp Thr Asp Arg Val Gln Phe Gly Pro Val Ala Leu Asn
465             470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Ser Ala Ala Gly Val Gly Met Leu Lys Gln Val Glu Ile Phe Thr
                515                 520                 525
Asn Gly Ser Cys Leu Gly Asn Pro Gly Pro Gly Tyr Gly Ala Ile
530                 535                 540
Leu Arg Tyr Arg Gly Arg Glu Lys Thr Phe Ser Ala Gly Tyr Thr Arg
545             550                 555                 560
Thr Thr Asn Asn Arg Met Gln Leu Met Ala Ala Ile Val Ala Leu Glu
                565                 570                 575
Ala Leu Lys Glu His Cys Glu Val Ile Leu Ser Thr Asn Ser Gln Tyr
            580                 585                 590
Val Arg Gln Gly Ile Thr Gln Trp Ile His Asn Trp Lys Lys Arg Gly
                595                 600                 605
Trp Lys Thr Ala Asp Lys Lys Pro Val Lys Asn Val Asp Leu Trp Gln
            610                 615                 620
Arg Leu Asp Ala Ala Leu Gly Gln His Gln Ile Lys Trp Glu Trp Val
625                 630                 635                 640
Lys Gly His Ala Gly His Pro Glu Asn Glu Arg Cys Asp Glu Leu Ala
                645                 650                 655
Arg Ala Ala Ala Met Asn Pro Thr Leu Glu Asp Thr Gly Tyr Gln Val
            660                 665                 670
Glu Val

<210> SEQ ID NO 3
<211> LENGTH: 1974
<212> TYPE: DNA
<213> ORGANISM: Artificial Sequence
<220> FEATURE:
<223> OTHER INFORMATION: Fusion Reverse Transcriptase (MMLV RT with
      RNase H domain deleted-Linker-RNaseH (Bacillus))
<220> FEATURE:
<221> NAME/KEY: CDS
<222> LOCATION: (1)..(1974)

<400> SEQUENCE: 3 atg acc ctg aac atc gaa gat gaa cat cgt ctg cat gaa acc agc aaa    48
Met Thr Leu Asn Ile Glu Asp Glu His Arg Leu His Glu Thr Ser Lys
1               5                   10                  15 gaa ccg gat gtg agc ctg ggc agc acc tgg ctg tct gat ttt ccg cag    96
Glu Pro Asp Val Ser Leu Gly Ser Thr Trp Leu Ser Asp Phe Pro Gln
            20                  25                  30 gcg tgg gcg gaa acc ggc ggt atg ggt ctg gcc gtt cgt cag gcg ccg   144
Ala Trp Ala Glu Thr Gly Gly Met Gly Leu Ala Val Arg Gln Ala Pro
        35                  40                  45 ctg att att ccg ctg aaa gcg acc agc acc ccg gtg agc att aaa cag   192
Leu Ile Ile Pro Leu Lys Ala Thr Ser Thr Pro Val Ser Ile Lys Gln
50                  55                  60 tat ccg atg agc cag gaa gcg cgt ctg ggc att aaa ccg cat att cag   240
Tyr Pro Met Ser Gln Glu Ala Arg Leu Gly Ile Lys Pro His Ile Gln
65                  70                  75                  80 cgt ctg ctg gat cag ggc att ctg gtg ccg tgt cag agc ccg tgg aac   288
```

```
               Arg Leu Leu Asp Gln Gly Ile Leu Val Pro Cys Gln Ser Pro Trp Asn
                           85                  90                  95 acc ccg ctg ctg ccg gtg aaa aaa ccg ggc acc aac gat tat cgt ccg      336
Thr Pro Leu Leu Pro Val Lys Lys Pro Gly Thr Asn Asp Tyr Arg Pro
            100                 105                 110 gtg cag gat ctg cgt gaa gtg aac aaa cgt gtg gaa gat att cat ccg      384
Val Gln Asp Leu Arg Glu Val Asn Lys Arg Val Glu Asp Ile His Pro
            115                 120                 125 acc gtg ccg aat ccg tat aac ctg ctg tct ggc ctg ccg ccg agc cat      432
Thr Val Pro Asn Pro Tyr Asn Leu Leu Ser Gly Leu Pro Pro Ser His
        130                 135                 140 cag tgg tat acc gtg ctg gat ctg aaa gat gcg ttt ttt tgc ctg cgt      480
Gln Trp Tyr Thr Val Leu Asp Leu Lys Asp Ala Phe Phe Cys Leu Arg
145                 150                 155                 160 ctg cat ccg acc agc cag ccg ctg ttt gcg ttt gaa tgg cgt gat ccg      528
Leu His Pro Thr Ser Gln Pro Leu Phe Ala Phe Glu Trp Arg Asp Pro
                165                 170                 175 gaa atg ggc att agc ggc cag ctg acc tgg acc cgt ctg ccg cag ggc      576
Glu Met Gly Ile Ser Gly Gln Leu Thr Trp Thr Arg Leu Pro Gln Gly
                180                 185                 190 ttt aaa aac agc ccg acc ctg ttt gat gaa gcg ctg cat cgt gat ctg      624
Phe Lys Asn Ser Pro Thr Leu Phe Asp Glu Ala Leu His Arg Asp Leu
                195                 200                 205 gcc gat ttt cgt att cag cat ccg gat ctg att ctg ctg cag tat gtg      672
Ala Asp Phe Arg Ile Gln His Pro Asp Leu Ile Leu Leu Gln Tyr Val
        210                 215                 220 gat gat ctg ctg ctg gcc gcg acc agc gaa ctg gat tgc cag cag ggc      720
Asp Asp Leu Leu Leu Ala Ala Thr Ser Glu Leu Asp Cys Gln Gln Gly
225                 230                 235                 240 acc cgt gcg ctg ctg cag acc ctg ggc aac ctg ggc tat cgt gcg agc      768
Thr Arg Ala Leu Leu Gln Thr Leu Gly Asn Leu Gly Tyr Arg Ala Ser
                245                 250                 255 gcg aaa aaa gcg cag att tgc cag aaa cag gtg aaa tat ctg ggc tat      816
Ala Lys Lys Ala Gln Ile Cys Gln Lys Gln Val Lys Tyr Leu Gly Tyr
                260                 265                 270 ctg ctg aaa gaa ggc cag cgt tgg ctg acc gaa gcg cgt aaa gaa acc      864
Leu Leu Lys Glu Gly Gln Arg Trp Leu Thr Glu Ala Arg Lys Glu Thr
            275                 280                 285 gtg atg ggc cag ccg acc ccg aaa acc ccg cgt cag ctg cgt gaa ttt      912
Val Met Gly Gln Pro Thr Pro Lys Thr Pro Arg Gln Leu Arg Glu Phe
        290                 295                 300 ctg ggc acc gcg ggc ttt tgc cgt ctg tgg att ccg ggc ttt gcg gaa      960
Leu Gly Thr Ala Gly Phe Cys Arg Leu Trp Ile Pro Gly Phe Ala Glu
305                 310                 315                 320 atg gcg gcg ccg ctg tat ccg ctg acc aaa acc ggc acc ctg ttt aac     1008
Met Ala Ala Pro Leu Tyr Pro Leu Thr Lys Thr Gly Thr Leu Phe Asn
                325                 330                 335 tgg ggt ccg gat cag cag aaa gcg tat cag gaa att aaa cag gcg ctg     1056
Trp Gly Pro Asp Gln Gln Lys Ala Tyr Gln Glu Ile Lys Gln Ala Leu
            340                 345                 350 ctg acc gcg ccg gcg ctg ggt ctg ccg gat ctg acc aaa ccg ttt gaa     1104
Leu Thr Ala Pro Ala Leu Gly Leu Pro Asp Leu Thr Lys Pro Phe Glu
        355                 360                 365 ctg ttc gtg gat gaa aaa cag ggc tat gcg aaa ggc gtg ctg acc cag     1152
Leu Phe Val Asp Glu Lys Gln Gly Tyr Ala Lys Gly Val Leu Thr Gln
    370                 375                 380 aaa ctg ggc ccg tgg cgt cgt ccg gtt gcg tat ctg agc aaa aaa ctg     1200
Lys Leu Gly Pro Trp Arg Arg Pro Val Ala Tyr Leu Ser Lys Lys Leu
385                 390                 395                 400
```

```
gat ccg gtt gcg gcg ggt tgg ccg ccg tgt ctg cgc atg gtt gcg gcg       1248
Asp Pro Val Ala Ala Gly Trp Pro Pro Cys Leu Arg Met Val Ala Ala
            405                 410                 415 att gcg gtg ctg acc aaa gat gcg ggc aaa ctg acc atg ggc cag ccg       1296
Ile Ala Val Leu Thr Lys Asp Ala Gly Lys Leu Thr Met Gly Gln Pro
        420                 425                 430 ctg gtg att ctg gcc ccg cat gca gtg gaa gcg ctg gtg aaa cag ccg       1344
Leu Val Ile Leu Ala Pro His Ala Val Glu Ala Leu Val Lys Gln Pro
    435                 440                 445 ccg gat cgt tgg ctg tct aac gcg cgt atg acc cat tat cag gcc ctg       1392
Pro Asp Arg Trp Leu Ser Asn Ala Arg Met Thr His Tyr Gln Ala Leu
450                 455                 460 ctg ctg gat acc gat cgt gtg cag ttt ggc ccg gtg gtg gcg ctg aat       1440
Leu Leu Asp Thr Asp Arg Val Gln Phe Gly Pro Val Val Ala Leu Asn
465                 470                 475                 480 ccg gcg acc ctg ctg ccg ctg ccg gaa gaa ggc ctg cag cat aac tgc       1488
Pro Ala Thr Leu Leu Pro Leu Pro Glu Glu Gly Leu Gln His Asn Cys
            485                 490                 495 ctg gat atc ctg gcc gaa gcg cat ggc acc cgt ccg gat ctg acc gat       1536
Leu Asp Ile Leu Ala Glu Ala His Gly Thr Arg Pro Asp Leu Thr Asp
        500                 505                 510 cag agc gcg gcg ggc gtg ggc gcg aaa gaa gaa att att tgg gaa agc       1584
Gln Ser Ala Ala Gly Val Gly Ala Lys Glu Glu Ile Ile Trp Glu Ser
    515                 520                 525 ctg agc gtg gat gtg ggc agc cag ggc aac ccg ggc att gtg gaa tat       1632
Leu Ser Val Asp Val Gly Ser Gln Gly Asn Pro Gly Ile Val Glu Tyr
530                 535                 540 aaa ggc gtg gat acc aaa acc ggc gaa gtg ctg ttt gaa cgc gaa ccg       1680
Lys Gly Val Asp Thr Lys Thr Gly Glu Val Leu Phe Glu Arg Glu Pro
545                 550                 555                 560 att ccg att ggc acc aac aac atg ggc cag ttt ctg gcg att gtg cat       1728
Ile Pro Ile Gly Thr Asn Asn Met Gly Gln Phe Leu Ala Ile Val His
            565                 570                 575 ggc ctg cgc tat ctg aaa gaa cgc aac agc cgc aaa ccg att tat agc       1776
Gly Leu Arg Tyr Leu Lys Glu Arg Asn Ser Arg Lys Pro Ile Tyr Ser
        580                 585                 590 aac agc cag acc gcg att aaa tgg gtg aaa gat aaa aaa gcg aaa agc       1824
Asn Ser Gln Thr Ala Ile Lys Trp Val Lys Asp Lys Lys Ala Lys Ser
    595                 600                 605 acc ctg gtg cgc aac gaa gaa acc gcg ctg att tgg aaa ctg gtg gat       1872
Thr Leu Val Arg Asn Glu Glu Thr Ala Leu Ile Trp Lys Leu Val Asp
610                 615                 620 gaa gcg gaa gaa tgg ctg aac acc cat acc tat gaa acc ccg att ctg       1920
Glu Ala Glu Glu Trp Leu Asn Thr His Thr Tyr Glu Thr Pro Ile Leu
625                 630                 635                 640 aaa tgg cag acc gat aaa tgg ggc gaa att aaa gcg gat tat ggc cgc       1968
Lys Trp Gln Thr Asp Lys Trp Gly Glu Ile Lys Ala Asp Tyr Gly Arg
            645                 650                 655 aaa taa                                                                1974
Lys

<210> SEQ ID NO 4
<211> LENGTH: 657
<212> TYPE: PRT
<213> ORGANISM: Artificial Sequence
<220> FEATURE:
<223> OTHER INFORMATION: Synthetic Construct

<400> SEQUENCE: 4

Met Thr Leu Asn Ile Glu Asp Glu His Arg Leu His Glu Thr Ser Lys
1               5                   10                  15
```

```
Glu Pro Asp Val Ser Leu Gly Ser Thr Trp Leu Ser Asp Phe Pro Gln
         20                  25                  30

Ala Trp Ala Glu Thr Gly Gly Met Gly Leu Ala Val Arg Gln Ala Pro
         35                  40                  45

Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
             85                  90                  95

Thr Pro Leu Leu Pro Val Lys Lys Pro Gly Thr Asn Asp Tyr Arg Pro
             100                 105                 110

Val Gln Asp Leu Arg Glu Val Asn Lys Arg Val Glu Asp Ile His Pro
             115                 120                 125

Thr Val Pro Asn Pro Tyr Asn Leu Leu Ser Gly Leu Pro Pro Ser His
     130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                 165                 170                 175

Glu Met Gly Ile Ser Gly Gln Leu Thr Trp Thr Arg Leu Pro Gln Gly
             180                 185                 190

Phe Lys Asn Ser Pro Thr Leu Phe Asp Glu Ala Leu His Arg Asp Leu
         195                 200                 205

Ala Asp Phe Arg Ile Gln His Pro Asp Leu Ile Leu Leu Gln Tyr Val
         210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                 245                 250                 255

Ala Lys Lys Ala Gln Ile Cys Gln Lys Gln Val Lys Tyr Leu Gly Tyr
             260                 265                 270

Leu Leu Lys Glu Gly Gln Arg Trp Leu Thr Glu Ala Arg Lys Glu Thr
         275                 280                 285

Val Met Gly Gln Pro Thr Pro Lys Thr Pro Arg Gln Leu Arg Glu Phe
         290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                 325                 330                 335

Trp Gly Pro Asp Gln Gln Lys Ala Tyr Gln Glu Ile Lys Gln Ala Leu
             340                 345                 350

Leu Thr Ala Pro Ala Leu Gly Leu Pro Asp Leu Thr Lys Pro Phe Glu
         355                 360                 365

Leu Phe Val Asp Glu Lys Gln Gly Tyr Ala Lys Gly Val Leu Thr Gln
         370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                 405                 410                 415

Ile Ala Val Leu Thr Lys Asp Ala Gly Lys Leu Thr Met Gly Gln Pro
                 420                 425                 430
```

-continued

```
Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Ser Ala Ala Gly Val Gly Ala Lys Glu Glu Ile Ile Trp Glu Ser
        515                 520                 525

Leu Ser Val Asp Val Gly Ser Gln Gly Asn Pro Gly Ile Val Glu Tyr
    530                 535                 540

Lys Gly Val Asp Thr Lys Thr Gly Glu Val Leu Phe Glu Arg Glu Pro
545                 550                 555                 560

Ile Pro Ile Gly Thr Asn Asn Met Gly Gln Phe Leu Ala Ile Val His
                565                 570                 575

Gly Leu Arg Tyr Leu Lys Glu Arg Asn Ser Arg Lys Pro Ile Tyr Ser
            580                 585                 590

Asn Ser Gln Thr Ala Ile Lys Trp Val Lys Asp Lys Ala Lys Ser
        595                 600                 605

Thr Leu Val Arg Asn Glu Glu Thr Ala Leu Ile Trp Lys Leu Val Asp
    610                 615                 620

Glu Ala Glu Glu Trp Leu Asn Thr His Thr Tyr Glu Thr Pro Ile Leu
625                 630                 635                 640

Lys Trp Gln Thr Asp Lys Trp Gly Glu Ile Lys Ala Asp Tyr Gly Arg
                645                 650                 655

Lys

<210> SEQ ID NO 5
<211> LENGTH: 155
<212> TYPE: PRT
<213> ORGANISM: Escherichia coli
<220> FEATURE:
<221> NAME/KEY: misc_feature
<223> OTHER INFORMATION: RNase H domain

<400> SEQUENCE: 5

Met Leu Lys Gln Val Glu Ile Phe Thr Asn Gly Ser Cys Leu Gly Asn
1               5                   10                  15

Pro Gly Pro Gly Gly Tyr Gly Ala Ile Leu Arg Tyr Arg Gly Arg Glu
                20                  25                  30

Lys Thr Phe Ser Ala Gly Tyr Thr Arg Thr Thr Asn Asn Arg Met Gln
            35                  40                  45

Leu Met Ala Ala Ile Val Ala Leu Glu Ala Leu Lys Glu His Cys Glu
        50                  55                  60

Val Ile Leu Ser Thr Asn Ser Gln Tyr Val Arg Gln Gly Ile Thr Gln
65                  70                  75                  80

Trp Ile His Asn Trp Lys Lys Arg Gly Trp Lys Thr Ala Asp Lys Lys
                85                  90                  95

Pro Val Lys Asn Val Asp Leu Trp Gln Arg Leu Asp Ala Ala Leu Gly
                100                 105                 110

Gln His Gln Ile Lys Trp Glu Trp Val Lys Gly His Ala Gly His Pro
        115                 120                 125
```

```
Glu Asn Glu Arg Cys Asp Glu Leu Ala Arg Ala Ala Ala Met Asn Pro
            130                 135                 140

Thr Leu Glu Asp Thr Gly Tyr Gln Val Glu Val
145                 150                 155

<210> SEQ ID NO 6
<211> LENGTH: 121
<212> TYPE: PRT
<213> ORGANISM: Bacillus
<220> FEATURE:
<221> NAME/KEY: misc_feature
<223> OTHER INFORMATION: RNase H domain

<400> SEQUENCE: 6

Ala Lys Glu Glu Ile Ile Trp Glu Ser Leu Ser Val Asp Val Gly Ser
1               5                   10                  15

Gln Gly Asn Pro Gly Ile Val Glu Tyr Lys Gly Val Asp Thr Lys Thr
            20                  25                  30

Gly Glu Val Leu Phe Glu Arg Glu Pro Ile Pro Ile Gly Thr Asn Asn
        35                  40                  45

Met Gly Gln Phe Leu Ala Ile Val His Gly Leu Arg Tyr Leu Lys Glu
    50                  55                  60

Arg Asn Ser Arg Lys Pro Ile Tyr Ser Asn Ser Gln Thr Ala Ile Lys
65                  70                  75                  80

Trp Val Lys Asp Lys Lys Ala Lys Ser Thr Leu Val Arg Asn Glu Glu
                85                  90                  95

Thr Ala Leu Ile Trp Lys Leu Val Asp Glu Ala Glu Glu Trp Leu Asn
            100                 105                 110

Thr His Thr Tyr Glu Thr Pro Ile Leu
        115                 120

<210> SEQ ID NO 7
<211> LENGTH: 6
<212> TYPE: PRT
<213> ORGANISM: Artificial Sequence
<220> FEATURE:
<223> OTHER INFORMATION: Linker connecting an RNase H domain to a
      polymerase domain
<220> FEATURE:
<221> NAME/KEY: CHAIN
<222> LOCATION: (1)..(6)

<400> SEQUENCE: 7

Ser Ala Ala Gly Val Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Linker connecting an RNase H domain to a
      polymerase domain
<220> FEATURE:
<221> NAME/KEY: CHAIN
<222> LOCATION: (1)..(6)

<400> SEQUENCE: 8

Ala Ala Ala Ala Ala Ala
1               5

<210> SEQ ID NO 9
<211> LENGTH: 18
<212> TYPE: PRT
```

-continued

```
<213> ORGANISM: Artificial Sequence
<220> FEATURE:
<223> OTHER INFORMATION: Linker connecting an RNase H domain to a
      polymerase domain
<220> FEATURE:
<221> NAME/KEY: CHAIN
<222> LOCATION: (1)..(18)

<400> SEQUENCE: 9

Ser Ala Ala Gly Val Gly Ala Ala Gly Gly Ala Ala Ser Ala Ala Gly
1               5                   10                  15

Val Gly
```